(12) United States Patent
Borgmann et al.

(10) Patent No.: US 7,495,133 B2
(45) Date of Patent: Feb. 24, 2009

(54) METHOD FOR HYDROFORMYLATING OLEFINS IN THE PRESENCE OF ORGANOPHOSPHORIC COMPOUNDS

(75) Inventors: Cornelia Borgmann, Frankfurt (DE); Detlef Selent, Berlin (DE); Armin Boerner, Rostock (DE); Klaus-Diether Wiese, Haltern (DE); Dagmara Ortmann, Brig (CH); Oliver Moeller, Recklinghausen (DE); Dieter Hess, Marl (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/593,330

(22) PCT Filed: Jan. 27, 2005

(86) PCT No.: PCT/EP2005/050347

§ 371 (c)(1),
(2), (4) Date: Jun. 11, 2007

(87) PCT Pub. No.: WO2005/090276

PCT Pub. Date: Sep. 29, 2005

(65) Prior Publication Data

US 2007/0282130 A1    Dec. 6, 2007

(30) Foreign Application Priority Data

Mar. 19, 2004  (DE) ............ 10 2004 013 514

(51) Int. Cl.
*C07C 45/50*  (2006.01)

(52) U.S. Cl. ............................. 568/451; 568/454

(58) Field of Classification Search .......... 568/451, 568/454
See application file for complete search history.

(56) References Cited

U.S. PATENT DOCUMENTS

| | | | |
|---|---|---|---|
| 4,599,206 A | 7/1986 | Billig et al. | |
| 5,093,534 A | 3/1992 | Ludwig et al. | |
| 6,015,928 A | 1/2000 | Gubisch et al. | |
| 6,184,424 B1 | 2/2001 | Bueschken et al. | |
| 6,239,318 B1 | 5/2001 | Schuler et al. | |
| 6,331,657 B1 | 12/2001 | Kaizik et al. | |
| 6,403,836 B2 | 6/2002 | Kaizik et al. | |
| 6,403,837 B1 | 6/2002 | Hess et al. | |
| 6,407,295 B1 | 6/2002 | Kaizik et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Röttger et al. | |
| 6,627,782 B2 | 9/2003 | Kaizik et al. | |
| 6,664,427 B1 * | 12/2003 | Burke et al. | 568/454 |
| 6,680,414 B2 | 1/2004 | Knoop et al. | |
| 6,720,457 B2 | 4/2004 | Drees et al. | |
| 6,818,770 B2 | 11/2004 | Selent et al. | |
| 6,924,389 B2 | 8/2005 | Jackstell et al. | |
| 6,956,133 B2 | 10/2005 | Jackstell et al. | |
| 6,960,699 B2 | 11/2005 | Totsch et al. | |
| 7,009,068 B2 | 3/2006 | Schmutzler et al. | |
| 7,026,523 B2 | 4/2006 | Rottger et al. | 585/638 |
| 7,109,346 B2 | 9/2006 | Beller et al. | |
| 7,115,790 B2 | 10/2006 | Beller et al. | 585/324 |
| 2003/0144559 A1 | 7/2003 | Hess et al. | |
| 2003/0195368 A1 | 10/2003 | Rottger et al. | |
| 2004/0236133 A1 | 11/2004 | Selent et al. | |
| 2004/0238787 A1 | 12/2004 | Wiese et al. | |
| 2004/0242947 A1 | 12/2004 | Beller et al. | |
| 2005/0043279 A1 | 2/2005 | Selent et al. | |
| 2005/0171371 A1 | 8/2005 | Borner et al. | |
| 2005/0182277 A1 | 8/2005 | Totsch et al. | |
| 2005/0209455 A1 | 9/2005 | Boerner et al. | |
| 2005/0209489 A1 | 9/2005 | Moller et al. | |
| 2005/0234270 A1 | 10/2005 | Kaizik et al. | |
| 2005/0240039 A1 | 10/2005 | Rottger et al. | 554/1 |
| 2005/0256281 A1 | 11/2005 | Grund et al. | |
| 2006/0036121 A1 | 2/2006 | Kaizik et al. | |
| 2006/0089469 A1 | 4/2006 | Komarov et al. | |
| 2006/0128998 A1 | 6/2006 | Lueken et al. | |
| 2006/0129004 A1 | 6/2006 | Lueken et al. | |
| 2006/0161017 A1 | 7/2006 | Grass et al. | |
| 2006/0183936 A1 | 8/2006 | Grass et al. | |
| 2007/0149781 A1 | 6/2007 | Riermeier et al. | 544/337 |
| 2007/0197799 A1 | 8/2007 | Holz et al. | 549/3 |
| 2007/0282130 A1 | 12/2007 | Borgmann et al. | |

FOREIGN PATENT DOCUMENTS

WO    2004 020381    3/2004

OTHER PUBLICATIONS

U.S. Appl. No. 10/593,330, filed Sep. 19, 2006, Borgmann et al.
U.S. Appl. No. 11/574,063, filed Feb. 22, 2007, Nierlich et al.
U.S. Appl. No. 11/574,060, filed Feb. 22, 2007, Borgmann et al.
U.S. Appl. No. 11/574,018, filed Feb. 21, 2007, Borgmann et al.
U.S. Appl. No. 11/721,978, filed Jun. 16, 2007, Beller et al.
U.S. Appl. No. 10/593,330, filed Jun. 11, 2007, Borgman et al.
U.S. Appl. No. 11/908,343, filed Sep. 11, 2007, Holz et al.
U.S. Appl. No. 12/065,091, filed Feb. 28, 2008, Hess et al.
Kyoko Nozaki, "Unsymmetric Bidentate Ligands in Metal-Catalyzed Carbonylation of Alkenes", The Chemical Record, vol. 5, 376-384 (2005), The Japan Chemical Journal Forum and Wiley Periodicals, Inc.
Jordi Girones, et al., "Enantioselectivity in the Catalytic Hydroesterification of Acenaphthylene: Direct Evidence of the Racemization of Pd"-Alkyl Species by a Degenerate Substitution Equilibrium with $Pd^0L_n$), Chemical Communication, The Royal Society of Chemistry 2003, pp. 1776-1778.

(Continued)

*Primary Examiner*—Sikarl A Witherspoon
(74) *Attorney, Agent, or Firm*—Oblon, Spivak, McClelland, Maier & Neustadt, P.C.

(57) ABSTRACT

(EN) The invention relates to the use of novel organophosphoric compounds and metal complexes thereof in catalytic reactions, and to the hydroformylation of olefins in the presence of these compounds.

14 Claims, No Drawings

OTHER PUBLICATIONS

M. Dolors Miquel-Serrano, et al., "Recoverable Chiral Palladium—Sulfonated Diphosphine Catalysts for the Asymmetric Hydrocarboxylation of Vinyl Arenes", Tetrahedron: Asymmetry 10, (1999), pp. 4463-4467.
U.S. Appl. No. 10/584,148, filed Jun. 22, 2006, Ortmann et al.
U.S. Appl. No. 10/593,492, filed Sep. 19, 2006, Borgmann et al.
U.S. Appl. No. 10/584,492, filed Jun. 22, 2006, Ortmann et al.
U.S. Appl. No. 10/525,376, filed May 8, 2006, Moeller et al.
U.S. Appl. No. 09/708,646, filed Nov. 9, 2000, Hess et al.
U.S. Appl. No. 10/505,879, filed Sep. 3, 2004, Borgmann.
U.S. Appl. No. 11/494,741, filed Jul. 28, 2006, Kaizik et al.
U.S. Appl. No. 10/562,454, filed Aug. 18, 2006, Krissman et al.
U.S. Appl. No. 10/576,302, filed Apr. 19, 2006, Kaizik et al.
U.S. Appl. No. 10/588,762, filed Aug. 8, 2006, Wiese et al.

* cited by examiner

METHOD FOR HYDROFORMYLATING OLEFINS IN THE PRESENCE OF ORGANOPHOSPHORIC COMPOUNDS

The present invention relates to the use of novel organophosphorus compounds and metal complexes thereof in catalytic reactions and to the hydroformylation of olefins in the presence of these compounds.

Hydroformylation (known as the oxo process) refers to the reaction between an ethylenically unsaturated compound, carbon monoxide and hydrogen in the presence of a catalyst to give the aldehyde having one more carbon atom. Frequently, the catalysts used in these reactions are compounds of transition metals of groups 8 to 10 of the Periodic Table of the Elements, especially compounds of rhodium and of cobalt.

In comparison to the catalysis with cobalt compounds, hydroformylation with rhodium compounds generally offers the advantage of higher selectivity under milder reaction conditions and is thus usually more economically viable. In the rhodium-catalyzed hydroformylation, complexes which consist of rhodium and ligands having phosphorus, nitrogen or oxygen donor atoms, preferably of trivalent phosphorus compounds as ligands, are usually used. Known ligands are, for example, compounds from the classes of the phosphines, phosphites and phosphonites. An overview of hydroformylation of olefins can be found in B. CORNILS, W. A. HERRMANN, "Applied Homogeneous Catalysis with Organometallic Compounds", Vol. 1 & 2, VCH, Weinheim, N.Y., 1996.

Every catalyst system (cobalt or rhodium) has its specific advantages. Depending on the feedstock and target product, different catalyst systems consisting of metal and one or more ligands are used. When rhodium and triphenylphosphine are employed, it is possible to hydroformylate α-olefins at relatively low synthesis gas pressures. The phosphorus ligand used is generally triphenylphosphine in excess, a high ligand/rhodium ratio being required in order to increase the selectivity of the reaction to give the commercially desired n-aldehyde product. In order to increase the economic viability, it would be desirable to reduce the ligand excess with the same results.

U.S. Pat. Nos. 4,694,109 and 4,879,416 relate to bisphosphine ligands and to their use in the hydroformylation of olefins at low synthesis gas pressures. Particularly in the hydroformylation of propene, high activities and high n/i selectivities are achieved with ligands of this type.

WO 95/30680 describes further bidentate phosphine ligands and their use in catalysis, including in hydroformylation reactions.

Ferrocene-bridged bisphosphines are disclosed, for example, in U.S. Pat. Nos. 4,169,861, 4,201,714 and 4,193,943 as ligands for hydroformylations.

The disadvantage of bidentate phosphine ligands, like those listed above, is the relatively complicated preparation which reduces the economic viability of industrial processes. In addition, their activity generally decreases greatly in the case of relatively long-chain olefins and in the case of olefins having internal double bonds.

Rhodium-monophosphite complexes are suitable catalysts for the hydroformylation of branched olefins having internal double bonds, but the selectivity for terminally hydroformylated compounds is low. EP 0 155 508 discloses the use of bisarylene-substituted monophosphites in the rhodium-catalyzed hydroformylation of sterically hindered olefins, for example isobutene.

Rhodium-phosphite complexes catalyze the hydroformylation of linear olefins having terminal and internal double bonds to form predominantly terminally hydroformylated products, whereas branched olefins having internal double bonds are converted only to a slight degree. When these phosphites coordinate to a transition metal center, they give rise to catalysts of enhanced activity, but the lifetime performance of these catalyst systems, for reasons including the hydrolysis sensitivity of the phosphite ligands, is unsatisfactory. The use of substituted bisaryldiols as reactants for the phosphite ligands, as described in EP 0 214 622 or EP 0 472 071, allowed considerable improvements to be achieved.

Rhodium complexes of these ligands are active hydroformylation catalysts for α-olefins. U.S. Pat. Nos. 4,668,651, 4,748,261 and 4,885,401 describe polyphosphite ligands with which α-olefins, but also 2-butene, can be converted with good selectivity to the terminally hydroformylated products. In U.S. Pat. No. 5,312,996, bidentate ligands of this type are also used to hydroformylate butadiene.

In comparison to phosphine ligands, phosphite ligands generally feature higher activities. In addition, their usually simple and inexpensive preparation is advantageous.

Phosphorus compounds of the benzodiazaphosphorinone and benzoxazaphosphorinone type are well known in the literature (see Phosphorus Sulfur Silicon Relat. Elem. 2000, 162, 81-218). Their syntheses and reactivities with ketones, and also their complexation to transition metals, are described.

However, these compounds have not been used in catalysis, neither as ligands nor as metal complexes.

Neda et al. describe, in J. Fluorine Chem. 1995, 71, 65-74 the reaction of benzodiazaphosphorinone derivatives with fluorinated ketones under trimethylamine catalysis. However, the benzodiazaphosphorinone derivatives were not used in catalysis.

Fei et al. describe, in Z. Anorg. Allg. Chem. 2000, 626, 1763-1772 the synthesis of bisphosphorus ligands having benzodiazaphosphorinone units and complexation to Pt complexes. There was no report of use in catalysis.

Borkenhagen et al. report, in Z. Naturforsch. B Chem. Sci. 1996, 51, 1627-1638, chromium complexes having benzodiazaphosphorinone ligands. These compounds were not used in catalysis.

Neda et al. describe, in Phosphorus, Sulfur Silicon Relat. Elem. 1996, 113, 287-294, the synthesis of benzoxazaphosphorinones, and investigate the reactivity of these systems, but not in catalytic reactions.

Kuliev et al. investigated the reactivity of chlorobenzoxazaphosphorinones. The results are summarized in Zh. Obshch. Khim. 1986, 56, 2797-8. The compounds were not used in catalysis.

In Chem. Ber. 1994, 127, 1579-86, Neda et al. report, inter alia, 2,2'-[(1,1'-biphenyl)-2,2'-diylbis(oxy)]bisbenzoxazaphosphorinones and the complexation of gold. Neither the phosphorus compound itself nor the gold complex were used in catalysis.

U.S. Pat. No. 6,664,427 describes a hydroformylation process in which specific bidentate phosphorus ligands which have two trivalent phosphorus atoms which are bonded to an α-hydroxybenzamide or α-hydroxybenzimide group are used.

It was an object of the present invention to provide an improved process for hydroformylating olefins having at least one ethylenically unsaturated double bond. In the reaction of α olefins, the activity to give aldehydes shall be enhanced and, in the case of olefins having internal double bonds, both the activity and the regioselectivity to give terminal aldehydes shall be increased.

It has been found that, surprisingly, hydroformylations of olefins in the presence of heteroacylphosphites of the general formula (1)

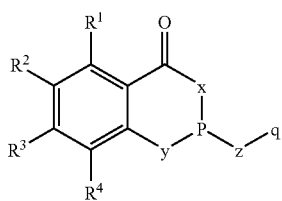

(1)

which do not have two α-hydroxybenzamide groups proceed in the desired improved manner.

The present invention therefore provides a process for hydroformylating olefins, comprising the reaction of a monoolefin or a monoolefin mixture having from 2 to 25 carbon atoms with a mixture of carbon monoxide and hydrogen in the presence of a heteroacylphosphite of the general formula (1) or a corresponding complex with one or more metals of groups 4 to 10 of the Periodic Table of the Elements

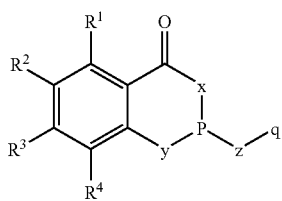

(1)

where $R^1$, $R^2$, $R^3$, $R^4$ and q are the same or different and are each a substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 70 carbon atoms, H, F, Cl, Br, I, —$CF_3$, —$CH_2(CF_2)_jCF_3$ where j=0-9, —$OR^5$, —$COR^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, —N=$CR^5R^6$, where $R^5$ and $R^6$ are the same or different and are each as defined for $R^1$, and M is an alkali metal, formally half an alkaline earth metal ion, an ammonium or phosphonium ion, x, y, z are each independently O, $NR^7$, S, where $R^7$ is as defined for q, and x, y, z are not simultaneously O, with the proviso that when q has a radical which has a structural unit (6c)

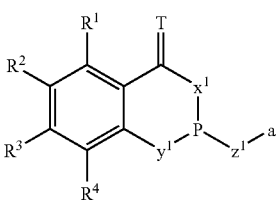

(6c)

where the $R^1$ to $R^4$ radicals are each as defined for formula (1), $x^1$, $y^1$, $z^1$ are each independently O, $NR^7$, S, where $R^7$ is as defined for q, T is an oxygen or an $NR^{30}$ radical, where $R^{30}$ is as defined for q, and the a position serves as the attachment point, x and $x^1$ must not simultaneously be N and x must not be N when T is $NR^{30}$.

In preferred embodiments, q, $R^1$, $R^2$, $R^3$ and $R^4$ are each as defined for hydrocarbon radicals, but the radicals are unsubstituted with a number of carbon atoms of from 1 to 50, in particular from 1 to 25.

Moreover, $R^5$, $R^6$ and $R^7$ are preferably each H, or an unsubstituted aliphatic or aromatic hydrocarbon radical having from 1 to 25 carbon atoms.

It is possible that two adjacent $R^1$ to $R^4$ ($R^1$ and $R^2$, $R^2$ and $R^3$, $R^3$ and $R^4$) radicals together form a fused substituted or unsubstituted aromatic, heteroaromatic, aliphatic, mixed aromatic-aliphatic or mixed heteroaromatic-aliphatic ring system.

In a preferred heteroacylphosphite of the formula (1), the q radical is selected from aromatics or heteroaromatics which are unsubstituted or substituted by at least one radical selected from aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 25 carbon atoms, F, Cl, Br, I, —$CF_3$, —$CH_2(CF_2)_jCF_3$ where j=0-9, —$OR^5$, —$COR^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, or —N=$CR^5R^6$, where $R^5$, $R^6$ and M are each as defined above.

In a further process variant, a heteroacylphosphite of the formula (1) is used, whose q radical consists of the —W—R radicals where W is a divalent substituted or unsubstituted aliphatic, alicyclic, mixed aliphatic-alicyclic, heterocyclic, mixed aliphatic-heterocyclic, aromatic, heteroaromatic, mixed aliphatic-aromatic hydrocarbon radical having from 1 to 50 carbon atoms, and the R radical is an —$OR^5$, —$NR^5R^6$, phosphite, phosphonite, phosphinite, phosphine or heteroacylphosphite or a radical of the formula (6c), where $R^5$ and $R^6$ are the same or different and are as defined for $R^1$, but are preferably each independently H, unsubstituted aliphatic and aromatic hydrocarbon radical having from 1 to 25 carbon atoms.

In a heteroacylphosphite of the formula (1) used with preference, which has a q radical with —W—R, W is a radical of the formula (2)

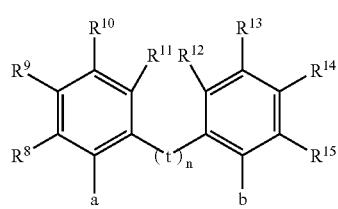

(2)

where $R^8$, $R^9$, $R^{10}$, $R^{11}$, $R^{12}$, $R^{13}$, $R^{14}$ and $R^{15}$ are the same or different and are each as defined for q, preferably each independently a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —$CF_3$, —$CH_2(CF_2)_jCF_3$ with j=0-9, —$OR^5$, —$COR^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, —N=$CR^5R^6$, where $R^5$ and $R^6$ are each independently selected from H, monovalent substituted or unsubstituted, aliphatic and aromatic hydrocarbon radicals having from 1 to 25 carbon atoms, and M is an alkali metal ion, formally half an alkaline earth metal ion, ammonium or phosphonium ion.

t is a $CR^{16}R^{17}$, $SiR^{16}R^{17}$, $NR^{16}$, O or S radical. $R^{16}$ and $R^{17}$ are as defined for $R^5$ and $R^6$, n is 0 or 1 and the a and b positions serve as attachment points.

It is possible that two adjacent $R^8$ to $R^{15}$ radicals together form a fused substituted or unsubstituted, aromatic, heteroaromatic, aliphatic, mixed aromatic-aliphatic or mixed heteroaromatic-aliphatic ring system.

In a further heteroacylphosphite of the formula (1) usable in the process, W has the definition of the formula (3)

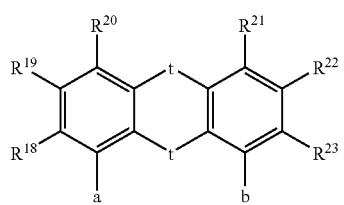

(3)

where $R^{18}$, $R^{19}$, $R^{20}$, $R^{21}$, $R^{22}$ and $R^{23}$ are the same or different and are each as defined for q, preferably each independently a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —$CF_3$, —$CH_2(CF_2)_jCF_3$ with j=0-9, —$OR^5$, —$COR^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, —$N$=$CR^5R^6$, where $R^5$ and $R^6$ are each independently selected from H, monovalent substituted or unsubstituted, aliphatic and aromatic hydrocarbon radicals having from 1 to 25 carbon atoms, and M is an alkali metal ion, formally half an alkaline earth metal ion, ammonium or phosphonium ion.

The a and b positions in the formulae 2 and 3 serve as attachment points to the R radical and to z as per formula (1).

t is a $CR^{16}R^{17}$, $SiR^{16}R^{17}$, $NR^{16}$, O or S radical, where $R^{16}$ and $R^{17}$ are as defined for $R^5$ and $R^6$ and the a and b positions serve as attachment points.

Again, it is possible that two adjacent $R^{18}$ to $R^{23}$ radicals together form a fused substituted or unsubstituted, aromatic, heteroaromatic, aliphatic, mixed aromatic-aliphatic or mixed heteroaromatic-aliphatic ring system.

In a further variant of the process according to the invention, in the case of the heteroacylphosphites of the formula (1) which have a q radical with —W—R, the W may be a radical of the formula (4)

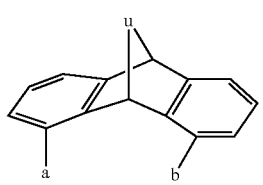

(4)

where u is a divalent group selected from radicals of the formulae (5a), (5b) and (5c)

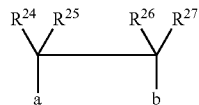

(5a)

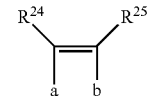

(5b)

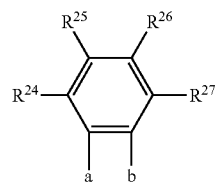

(5c)

in which $R^{24}$, $R^{25}$, $R^{26}$ and $R^{27}$ are the same or different and are each as defined for q, preferably each independently a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —$CF_3$, —$CH_2(CF_2)_jCF_3$ with j=0-9, —$OR^5$, —$COR^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, —$N$=$CR^5R^6$, where $R^5$ and $R^6$ are each independently selected from H, monovalent substituted or unsubstituted, aliphatic and aromatic hydrocarbon radicals having from 1 to 25 carbon atoms, and M is an alkali metal ion, formally half an alkaline earth metal ion, ammonium or phosphonium ion, and the a and b positions serve as attachment points for u.

Here too, it is possible that two adjacent $R^{24}$ to $R^{27}$ radicals together form a fused substituted or unsubstituted, aromatic, heteroaromatic, aliphatic, mixed aromatic-aliphatic or mixed heteroaromatic-aliphatic ring system.

In a heteroacylphosphite of the formula (1) used with preference, which has a q radical with —W—R, R represents radicals of the general formulae (6a), (6b) and (6c):

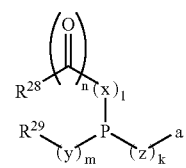

(6a)

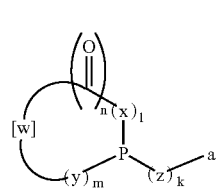

(6b)

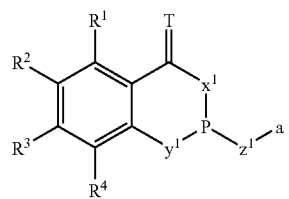
(6c)

where $R^{28}$ and $R^{29}$ are the same or different and are each independently as defined for $R^1$, but preferably a monovalent unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, m=0 or 1, n=0 or 1, k=0 or 1, l=0 or 1 and the a position serves as the attachment point. $R^1$, $R^2$, $R^3$, $R^4$, q, W, x, y and z are each defined as specified and where the $R^1$ to $R^4$ radicals are each as defined for the formula (1), $x^1$, $y^1$, $z^1$ are each independently O, $NR^7$, S, where $R^7$ is as defined for q, T is an oxygen or an $NR^{30}$ radical where $R^{30}$ is as defined for q, the a position serves as the attachment point and, in the case that R is 6c, x and $x^1$ must not simultaneously be N and x must not be N when T is $NR^{30}$.

In each case two adjacent $R^{24}$ to $R^{27}$ radicals may together form a fused substituted or unsubstituted, aromatic, heteroaromatic, aliphatic, mixed aromatic-aliphatic or mixed heteroaromatic-aliphatic ring system.

The following phosphite ligands mentioned below by way of example may be used in the process according to the invention, where Me is a methyl group, $^t$Bu is a tert-butyl group and Ph is a phenyl group.

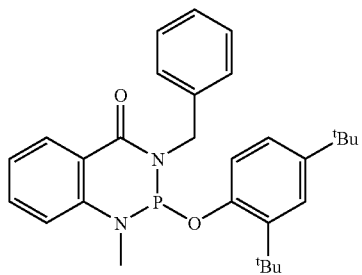
(A)

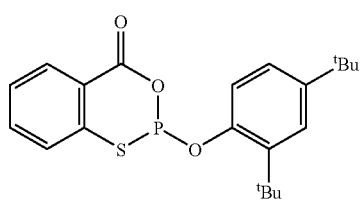
(B)

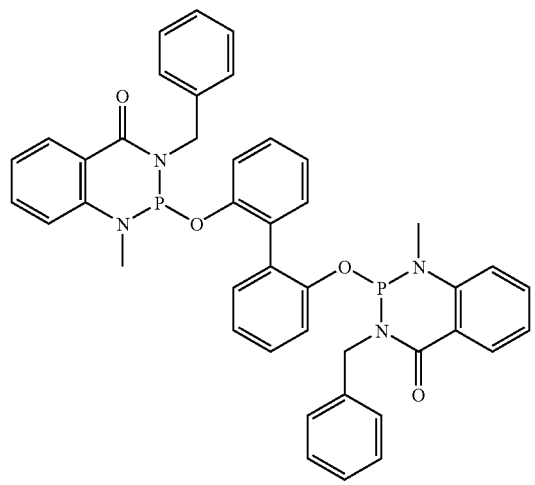
(C)

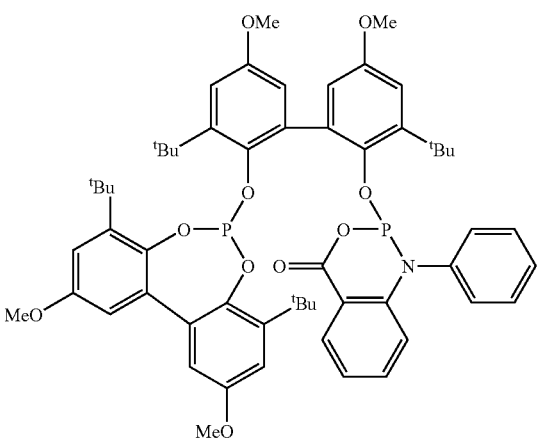
(D)

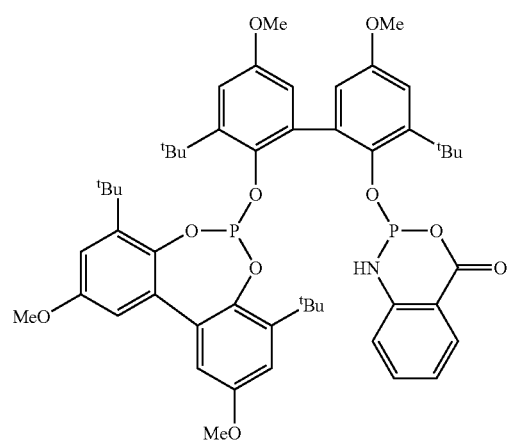
(E)

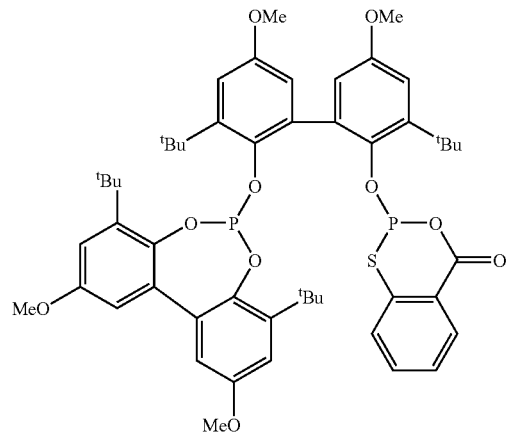
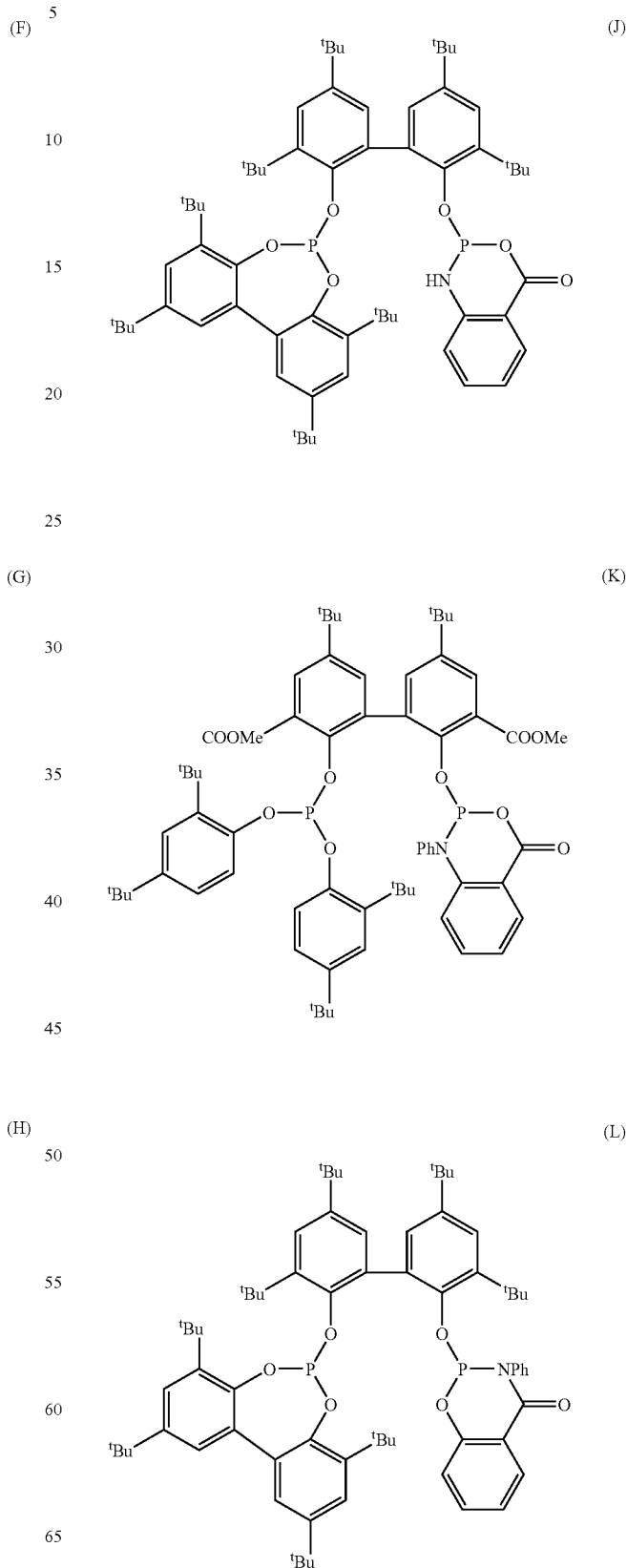

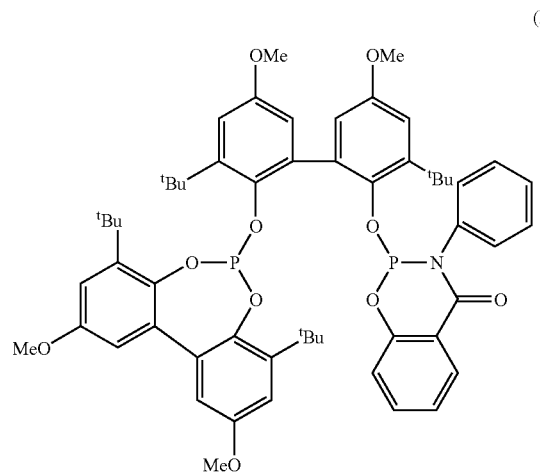
(M)
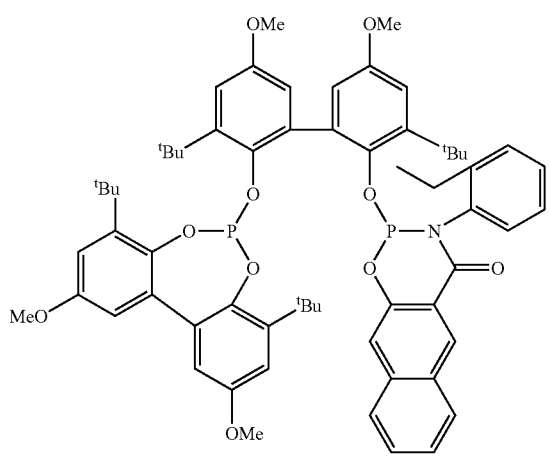
(P)
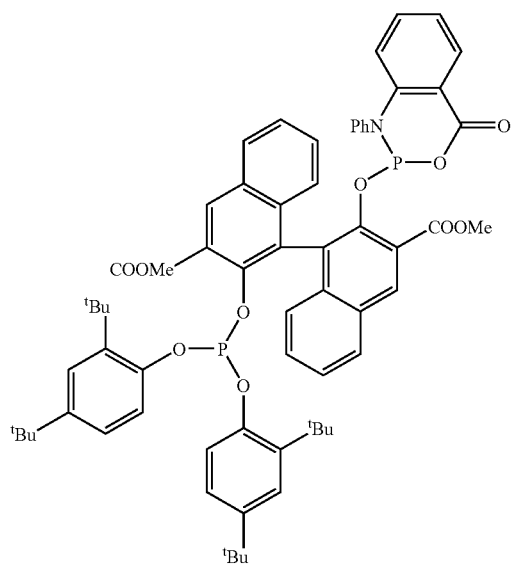
(N)
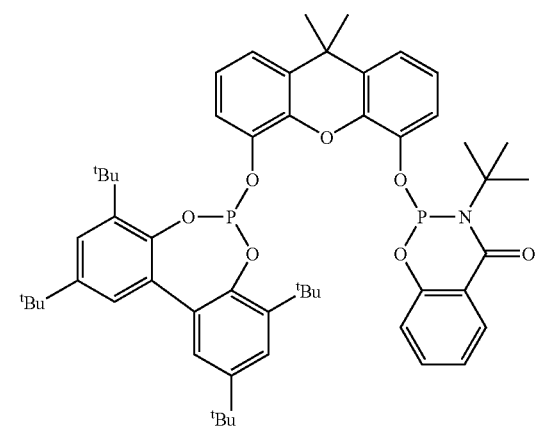
(Q)
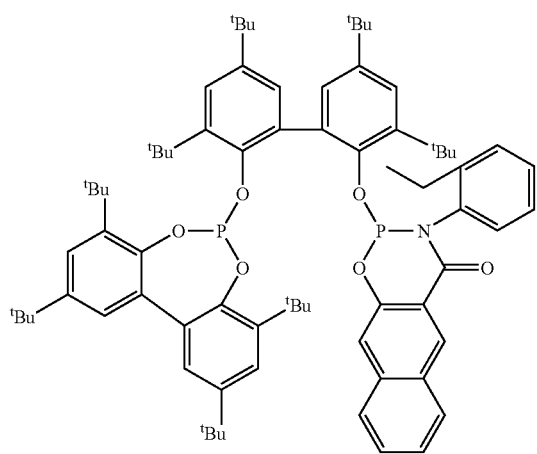
(O)
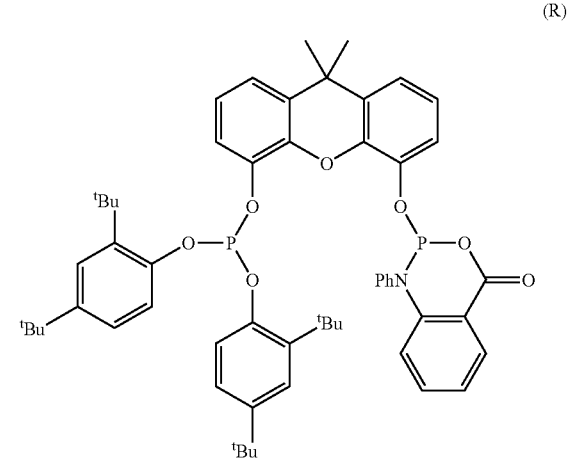
(R)

(S)
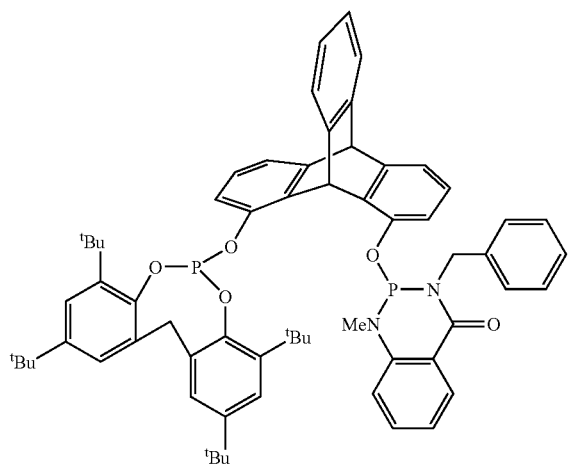

(T)
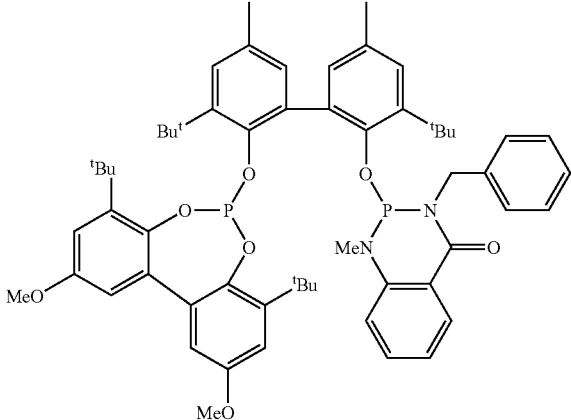

(U)
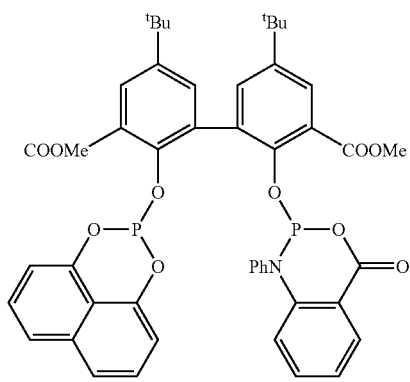

(V)
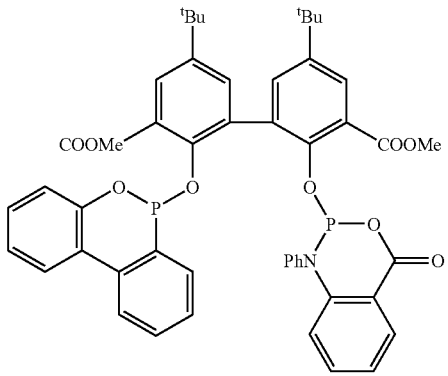

(W)
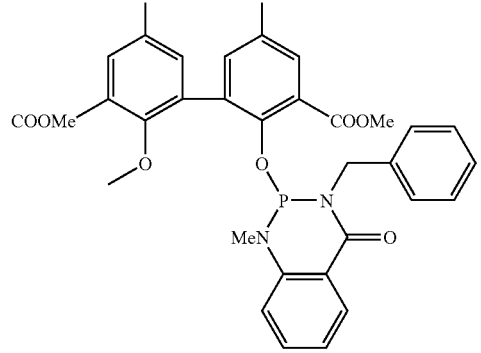

Heteroacylphosphites of the formula (1) can be prepared by a sequence of reactions of phosphorus halides with alcohols, amines, thiols, carboxylic acids, carboxamides, thiocarboxylic acids, α-hydroxyarylcarboxylic acids, α-hydroxyarylcarboxamides, α-hydroxyarylthiocarboxylic acids, α-aminoarylcarboxylic acids, α-aminoarylcarboxamides, α-aminoarylthiocarboxylic acids, α-mercaptoarylcarboxylic acids, α-mercaptoarylcarboxamides and/or α-mercaptoarylthiocarboxylic acids, in which halogen atoms on the phosphorus may be exchanged for oxygen, nitrogen and/or sulfur groups. The basic procedure is illustrated by way of example using a route to compounds of the general formula (1):

In a first step, a compound of the formula (1a) is reacted with a phosphorus trihalide $P(Hal)_3$, for instance $PCl_3$, $PBr_3$ and $PI_3$, preferably phosphorus trichloride $PCl_3$, without base or in presence of a base which is used in equivalent or catalytic amounts, to give the compound of the formula (1b).

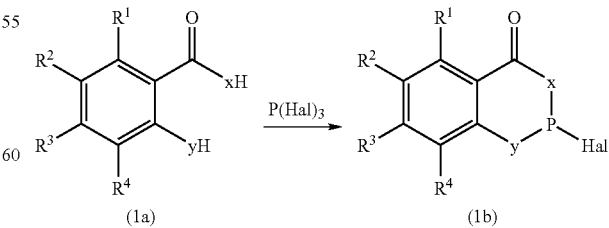

In a second reaction step, the desired heteroacylphosphite of the formula (1) is obtained from the compound (1b) by reaction with an alcohol HO-q or with an amine $HN(R^7)$-q or with a thiol HS-q without base or in the presence of a base which is used in equivalent or catalytic amounts.

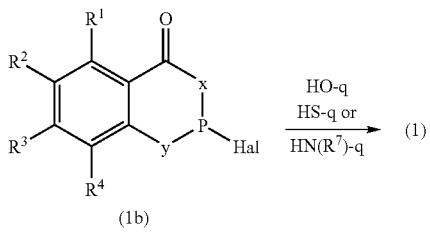

(1b)

The $R^1$ to $R^4$, $R^7$ and x, y and q radicals are each as already defined.

Since the alcohols, amines, thiols and carboxylic acid derivatives used and their subsequent products are frequently in solid form, the reactions are generally performed in solvents. The solvents used are aprotic solvents which react neither with the alcohols, amines, thiols or carboxylic acid derivatives nor with the phosphorus compounds. Suitable solvents are, for example, tetrahydrofuran, ethers such as diethyl ether or MTBE (methyl tert-butyl ether) or aromatic hydrocarbons such as toluene.

The reaction of phosphorus halides with alcohols, amines, thiols or carboxylic acid derivatives form hydrogen halide which escapes as a result of heating or is bound by added bases in equivalent or in catalytic amounts. Examples of bases are tertiary amines such as triethylamine, pyridine or N-methylpyrrolidinone. In some cases, it is also sensible to convert the alcohols to metal alkoxides before the reaction, for example by reaction with sodium hydride or butyllithium.

The solvents used must be very substantially water- and oxygen-free; preference is given to solvents having a water content of from 0 to 500 ppm, more preferably from 0 to 250 ppm. The water content can be determined, for example, by the Karl Fischer method.

The solvent can be dried by distilling the solvent over a suitable desiccant or by passing the solvent through a cartridge or column filled, for example, with 4 Å molecular sieves.

The synthesis steps preferably proceed at temperatures of from −80° C. to 150° C.; in most cases, it has been found to be useful to work at temperatures of from −20° C. to 110° C., more preferably at from 0° C. to 80° C.

In the process according to the invention, the metals of group 4, 5, 6, 7, 8, 9 or 10 of the Periodic Table of the Elements may be used. Examples of suitable metals are rhodium, cobalt, iridium, nickel, palladium, platinum, iron, ruthenium, osmium, chromium, molybdenum and tungsten. The metal used is more preferably rhodium. The catalyst metals may be introduced into the reaction in the form of salts or complexes; in the case of rhodium, for example, rhodium carbonyls, rhodium nitrate, rhodium chloride, $Rh(CO)_2$(acac) (acac=acetylacetonate), rhodium acetate, rhodium octanoate or rhodium nonanoate are suitable.

The active catalyst species forms under the reaction conditions from the heteroacylphosphite ligands of the formula (1) and the catalyst metal. In the hydroformylation, a carbonyl hydride-heteroacylphosphite complex is formed on contact with synthesis gas. The heteroacylphosphites and further ligands may be added to the reaction mixture in free form together with the catalyst metal (as a salt or complex), in order to obtain the active catalyst species in situ. It is also possible to use a heteroacylphosphite-metal complex, which comprises the abovementioned heteroacylphosphite ligands and the catalyst metal as a precursor for the actual catalytically active complex. These heteroacylphosphite-metal complexes are prepared by reacting the appropriate catalyst metal of groups 4 to 10 in elemental form or in the form of a chemical compound with the heteroacylphosphite ligand. It may be advantageous when heteroacylphosphite ligands of the formula (1) are used in excess, so that heteroacylphosphite ligands are present as the free ligand in the hydroformylation mixture.

In the process according to the invention, further ligands for the metal atom used in addition to the ligands of the formula (1) may be used.

Additional ligands present in the reaction mixture may be phosphorus ligands, preferably phosphines, bisphosphites, phosphonites or phosphinites.

Examples of such ligands are:

phosphines: triphenylphosphine, tris(p-tolyl)phosphine, tris(m-tolyl)phosphine, tris(o-tolyl)phosphine, tris(p-methoxyphenyl)phosphine, tris(p-dimethylaminophenyl)phosphine, tricyclohexylphosphine, tricyclopentylphosphine, triethylphosphine, tri(1-naphthyl)phosphine, tribenzylphosphine, tri-n-butylphosphine, tri-t-butylphosphine.

phosphites: trimethyl phosphite, triethyl phosphite, tri-n-propyl phosphite, tri-1-propyl phosphite, tri-n-butyl phosphite, tri-1-butyl phosphite, tri-t-butyl phosphite, tris(2-ethylhexyl)phosphite, triphenyl phosphite, tris(2,4-di-t-butylphenyl)phosphite, tris(2-t-butyl-4-methoxyphenyl) phosphite, tris(2-t-butyl-4-methylphenyl)phosphite, tris(p-cresyl)phosphite.

phosphonites: methyldiethoxyphosphine, phenyldimethoxyphosphine, phenyldiphenoxy-phosphine, 2-phenoxy-2H-dibenz[c,e][1,2]oxaphosphorin and derivatives thereof in which some or all of the hydrogen atoms have been replaced by alkyl and/or aryl radicals or halogen atoms.

Common phosphinite ligands are diphenyl(phenoxy)phosphine and its diphenyl(methoxy)-phosphine and diphenyl (ethoxy)phosphine derivatives.

The heteroacylphosphites or heteroacylphosphite-metal complexes may be used in processes for hydroformylating olefins, preferably having from 2 to 25 carbon atoms, more preferably from 6 to 12 and most preferably 8, 9, 10, 11 or 12 carbon atoms, to give the corresponding aldehydes. Preference is given here to using heteroacylphosphite complexes having metals of group 8 as the catalyst precursor.

Preference is given to using from 1 to 500 mol, preferably from 1 to 200 mol and more preferably from 2 to 50 mol of the inventive heteroacylphosphite per mole of metal of group 8 of the Periodic Table. Fresh heteroacylphosphite ligand may be added at any time in the reaction in order to keep the concentration of free heteroacylphosphite, i.e. not coordinated to the metal, constant.

The concentration of the metal in the reaction mixture is preferably in the range from 1 ppm to 1000 ppm, preferably in the range from 5 ppm to 300 ppm, based on the total weight of the reaction mixture.

The hydroformylation reactions performed with the heteroacylphosphites of the formula I or the corresponding metal complexes can be performed by known methods, as described, for example, in J. FALBE, "New Syntheses with Carbon Monoxide", Springer Verlag, Berlin, Heidelberg, New York, pages 95 ff., (1980). The olefin compound(s) is/are reacted in the presence of the catalyst with a mixture of CO and $H_2$ (synthesis gas) to give the aldehydes having one more carbon atom.

The reaction temperatures are preferably from 40° C. to 180° C. and preferentially from 75° C. to 140° C. The pressures under which the hydroformylation proceeds are preferably from 1 to 300 bar as synthesis gas and preferably from 10 to 64 bar. The molar ratio between hydrogen and carbon monoxide ($H_2$/CO) in the synthesis gas is preferably from 10/1 to 1/10 and preferentially from 1/1 to 2/1.

The catalyst or the ligand is dissolved homogeneously in the hydroformylation mixture consisting of reactants (olefins and synthesis gas) and products (aldehydes, alcohols, high boilers formed in the process). Optionally, a solvent can be used additionally.

Owing to their relatively high molecular weight, the heteroacylphosphites have low volatility. They can therefore be removed in a simple manner from the more volatile reaction products. They are sufficiently soluble in the common organic solvents.

The reactants for the hydroformylation are olefins or mixtures of olefins having from 2 to 25 carbon atoms with terminal or internal C=C double bonds. Preferred reactants are generally α-olefins such as propene, 1-butene, 2-butene, 1-hexene, 1-octene, and also dimers and trimers of butene (isomer mixtures).

The hydroformylation can be performed continuously or batchwise. Examples of industrial designs are stirred tanks, bubble columns, jet nozzle reactors, tubular reactors or loop reactors, some of which may be in the form of batteries and/or provided with internals.

The reaction can be effected continuously or in a plurality of stages. The separation of the aldehyde compounds formed and of the catalyst can be performed by a conventional method such as fractionation, extraction, nanofiltration with appropriate membranes. In industry, this can be done, for example, by means of a distillation, by means of a falling-film evaporator or a thin-film evaporator. This is true particularly when the catalyst, dissolved in a high-boiling solvent, is removed from the lower-boiling products. The removed catalyst solution can be used for further hydroformylations. When lower olefins are used (e.g. propene, butene, pentene), it is also possible to discharge the products from the reactor via the gas phase.

The present invention further provides processes for carbonylation, hydrocyanation, isomerization of olefins or amidocarbonylation in the presence of heteroacylphosphines of the formula (1) or complexes thereof with metals of groups 4 to 10 of the Periodic Table of the Elements, where $R^1$, $R^2$, $R^3$, $R^4$ and q are the same or different and are each a substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 70 carbon atoms, H, F, Cl, Br, I, —$CF_3$, —$CH_2(CF_2)_jCF_3$ where j=0-9, —$OR^5$, —$COR^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, —N=$CR^5R^6$, where $R^5$ and $R^6$ are the same or different and are each as defined for $R^1$, and M is an alkali metal ion, formally half an alkaline earth metal ion, an ammonium or phosphonium ion, x, y, z are each independently O, $NR^7$, S, where $R^7$ is as defined for $R^1$.

The q, $R^1$, $R^2$, $R^3$, $R^4$, x, y and z radicals are each defined as specified. The preferred variants of compounds of the formula (1) specified for the hydroformylation apply analogously to these reactions.

The examples which follow are intended to illustrate the present invention. In all examples, standard Schlenk technology under protective gas was employed. The solvents were dried over suitable desiccants before use.

EXAMPLE 1

Preparation of Ligand (D)

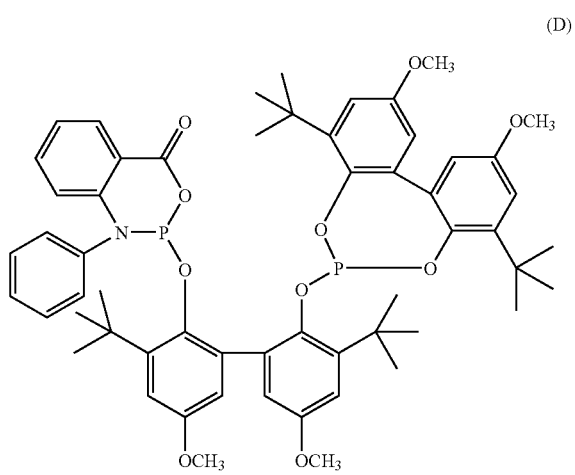

(D)

a) Preparation of the Cl Phosphorus Unit (Φ)

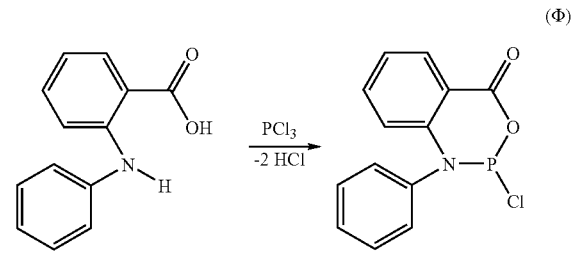

(Φ)

17.65 ml of a 5.315 M (represents molar, i.e. mol/l) standard solution of phosphorus trichloride in toluene (93.79 mmol) are slowly added dropwise at room temperature to a suspension of 20 g (93.79 mmol) of diphenylamine-2-carboxylic acid in toluene (80 ml). After the $PCl_3$ addition has ended, the mixture is heated slowly to 90° C. in a water bath. The mixture is stirred at this temperature until no further gas evolution is observed (approx. 5 h), heated under reflux for another 1 h and filtered. The filtercake is washed with 2×10 ml of cold toluene. The combined filtrates are concentrated to dryness under reduced pressure and taken up in 60 ml of dichloromethane. Filtration, evaporation of the solvent under reduced pressure and drying in an oil-pump vacuum give rise to the spectroscopically pure Cl—P compound (Φ) in the form of a dark red-brown syrupy liquid. Yield: 18.0 g (61%). $^{31}P\{^1H\}$ NMR ($CD_2Cl_2$) δ135.1 ppm.

b) Preparation of the Hydroxyphosphite Compound (Δ)

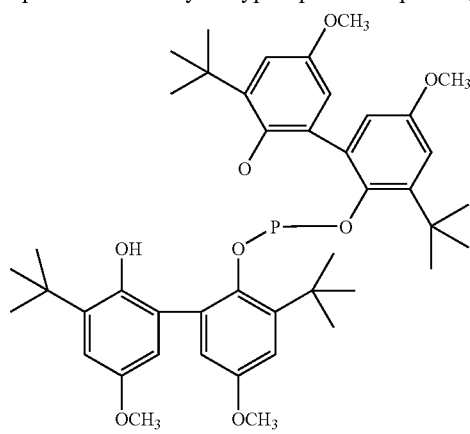

The compound (Δ) was prepared as described in EP 1 201 675 and as described in D. Selent, D. Hess, K.-D. Wiese, D. Röttger, C. Kunze, A. Börner, *Angew. Chem.* 2001, 113, 1739.

c) Preparation of (D)

11.4 ml of a 0.32 M (molar) solution of n-butyllithium in hexane (3.653 mmol) are added at −20° C. with stirring to a solution of 2.721 g (3.653 mmol) of the hydroxyphosphite (Δ) in THF (36 ml). The resulting mixture is added at room temperature slowly to a solution of 1.014 g (3.653 mmol) of the compound (Φ) described under a) in THF (15 ml). The red-brown solution is stirred for 4 h, the solvent is evaporated under reduced pressure and the resulting residue is stirred with hexane (60 ml). The mixture is filtered and the filtercake is extracted with diethyl ether (50 ml). The extraction solution is stored at 5° C. for 1 day and filtered, and the filtercake is washed with hexane (1×8 ml) and dried at 60° C. at 0.1 mbar for 2 h. Yield: 1.593 g (44%). Elemental analysis (calc. for $C_{57}H_{65}O_{10}P_2N=986.08$ g/mol): C, 68.73 (69.43); H, 6.76 (6.64); P, 6.09 (6.28); N, 1.48 (1.42)%. FAB-MS: m/e 985 (4%, M$^+$), 744 (30%), 727 (100%). $^{31}$P NMR (toluene-D8): δ 114.9 (d, $J_{PP}$=22.2 Hz), 117.4 (d, $J_{PP}$=5.5 Hz), 138.9 (d, $J_{PP}$=22.2 Hz), 141.2 (d, $J_{PP}$=5.5 Hz) ppm.

EXAMPLE 2

Preparation of Ligand (E)

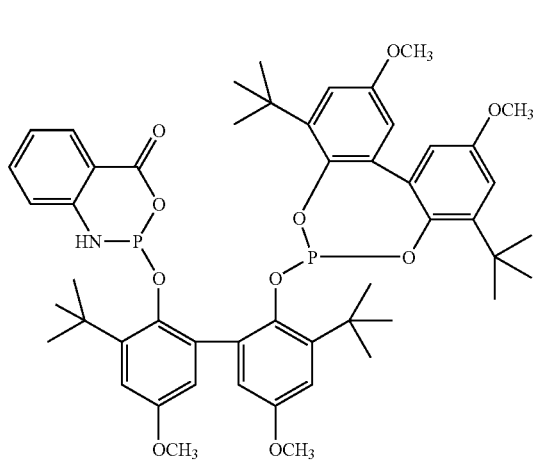

a) Preparation of Cl-phosphorus Unit (Γ)

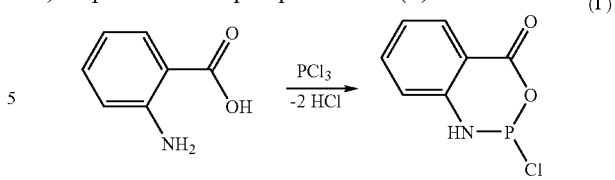

28.24 ml of a 5.315 M standard solution of phosphorus trichloride in toluene (145.84 mmol) are slowly added dropwise at room temperature to a suspension of 20 g (145.83 mmol) of anthranilic acid in toluene (105 ml). After the PCl$_3$ addition has ended, the mixture is heated slowly to 90° C. in a water bath. The mixture is stirred at this temperature until no further gas evolution is observed (approx. 5 h) and heated under reflux for another 1 h. Subsequently, the supernatant is decanted from the oily residue and the toluene is removed under reduced pressure. The residue is taken up in dichloromethane (80 ml), the mixture is filtered and the solution is concentrated to 50% of the starting volume. After storing at 5° C. for 3 days, the fine crystalline yellow substance formed is filtered off at −15° C. and then dried under reduced pressure at room temperature. Yield: 7.76 g (26%) of spectroscopically pure Cl—P compound. $^{31}$P{$^1$H} NMR (CD$_2$Cl$_2$) δ 135.1 ppm.

b) Preparation of the Hydroxyphosphite Compound (Δ)

For the preparation of (Δ) see the information on the synthesis of the ligand (D).

c) Preparation of (E)

4.1 g of hydroxyphosphite (Δ) (5.50 mmol) in THF (53 ml) are deprotonated at −20° C. with 3.44 ml of a 1.6 M solution of n-butyllithium (5.50 mmol). The solution of the lithium salt thus obtained is added dropwise with stirring to a solution of 1.108 g (5.50 mmol) of the compound (Γ) described under a) in THF (23 ml). After stirring at room temperature for 16 h, the mixture is concentrated to dryness under reduced pressure and the resulting residue is extracted with boiling hexane (80 ml) until only traces of (Δ) are present (recognizable by the sharp phosphorus signal at 140.7 ppm in CD$_2$Cl$_2$). The residue is extracted with diethyl ether (50 ml). The ether filtrate is concentrated to obtain 2.0 g (40%) of a yellow, spectroscopically pure solid. P analysis (calc. for $C_{51}H_{61}O_{10}NP_2$=909.99 g/mol): P, 6.95 (6.81)%. $^{31}$P{$^1$H} NMR (CD$_2$Cl$_2$): δ 118.0, 124.0, 136.2, 141.8 ppm. FAB-MS: e/m 910 (40%, M$^+$), 727 (100%).

EXAMPLE 3

Preparation of Ligand (H)

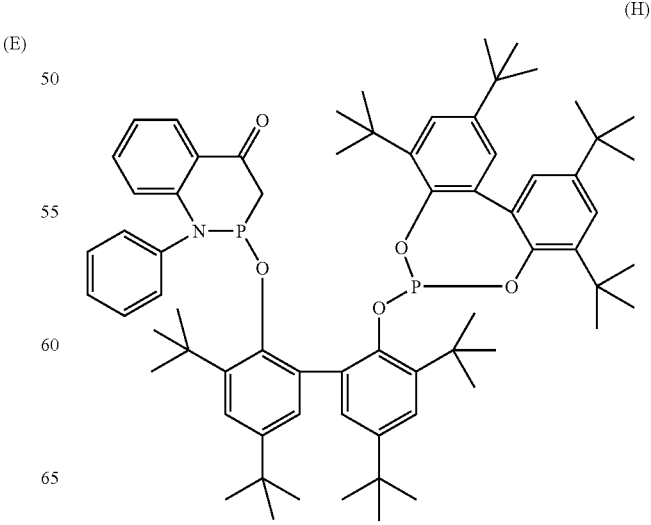

a) Preparation of the Cl-phosphorus Unit (Φ)

The Cl-phosphorus unit (Φ) is prepared as described under Example 1.

b) Preparation of the Hydroxyphosphite Compound (Σ)

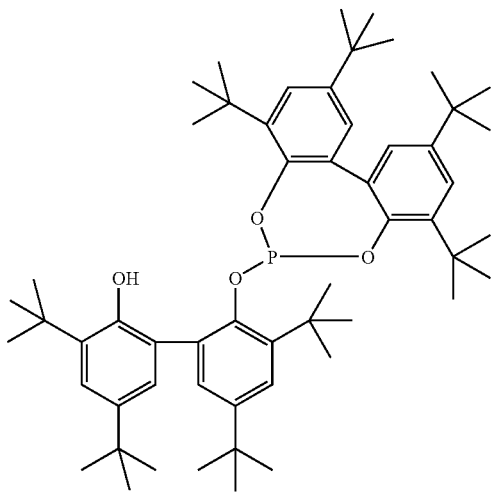

(Σ)

The compound (Σ) was prepared as described in EP 1 201 675 or as described in D. Selent, D. Hess, K.-D. Wiese, D. Röttger, C. Kunze, A. Börner, *Angew. Chem.* 2001, 113, 1739.

c) Preparation of Ligand (H)

The preparation is effected analogously to the synthesis of ligand (D). The reaction was effected with 2.518 g (2.97 mmol) of hydroxyphosphite (Σ), an equimolar amount of n-butyllithium, used as a 0.32 M solution in hexane, and 0.825 g (2.97 mmol) of compound (Φ) in a total of 50 ml of THF. After workup, 1.51 g (47% of theory) of the spectroscopically pure ligand (H) are isolated in the form of a light brown solid. Elemental analysis (calc. for $C_{69}H_{89}O_6P_2N$=1090.41 g/mol): C, 76.10 (76.00); H, 8.46 (8.23); N, 1.31 (1.29); P, 5.68 (5.68) %. $^{31}P\{^1H\}$ NMR ($CD_2Cl_2$): δ 113.1, 116.0, 141.7 ppm. CI-MS (isobutane): m/e 1090 (65%, M+), 832 (100%).

EXAMPLE 4

Preparation of Ligand (J)

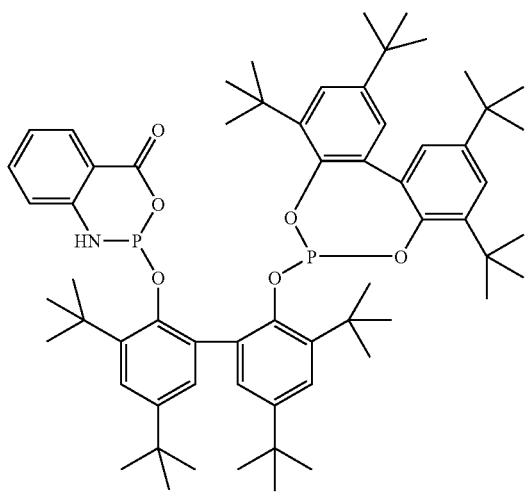

(J)

The preparation and workup were effected analogously to the synthesis of (E). Starting from 2.418 g (2.847 mmol) of hydroxyphosphite compound (Σ), an equimolar amount of n-butyllithium, used as 0.32 M solution in hexane, and 0.573 g (2.847 mmol) of the compound (Γ) used for the synthesis of (E) in a total of 55 ml of THF, 0.837 g (29% of theory) of the spectroscopically pure ligand (J) is isolated in the form of a yellow solid. Elemental analysis (calc. for $C_{63}H_{85}O_6P_2N$=1014.31 g/mol): C, 74.86 (74.60); H, 8.43 (8.45); N, 1.26 (1.38); P, 5.44 (6.10)%. $^{31}P\{^1H\}$ NMR ($CD_2Cl_2$): δ 119.5, 123.8, 140.0, 143.0 ppm. EI-MS: m/e 1015 (13%, M+), 833 (83%), 440 (100%).

HYDROFORMYLATION EXAMPLES 5 TO 15

The hydroformylation experiments were performed in a 200 ml autoclave from Buddeberg, Mannheim, equipped with a pressure-maintaining device, gas flow meter, sparging stirrer and pressure pipette. For the experiments, the following solutions of rhodium in the form of [acacRh(COD)] (acac=acetylacetonate anion, COD=cycloocta-1,5-diene) as the catalyst precursor in toluene were introduced into the autoclave under an argon atmosphere: for experiments with 14 ppm by mass of rhodium, 10 ml of a 0.604 mM solution; for experiments with 28 ppm by mass of rhodium, 20 ml of a 0.604 mM solution; for experiments with 140 ppm by mass of rhodium, 10 ml of a 6.04 mM solution. Subsequently, the appropriate amount of the phosphate compounds dissolved in toluene, generally 5 ligand equivalents per rhodium, was added. Addition of further toluene adjusted the starting volume of the catalyst solution to 41 ml for the reaction with 1-octene and the n-octenes (=mixture of 1-octene, 2-octene, 3-octene and 4-octene with approx. 3% 1-octene fraction) and to 51.5 ml for the reaction with 2-pentene. 15 ml of 1-octene or n-octenes or 4.5 ml of 2-pentene were introduced into the pressure pipette; the mass of the olefin had been determined beforehand. After exchange of the argon atmosphere by purging with synthesis gas ($CO/H_2$=1:1), the autoclave was heated at a synthesis gas pressure of 11-13 bar (33 bar for 1-octene) with stirring (1500 rpm) to the following temperatures:

a) experiments with 1-octene: 100° C.,
b) experiments with n-octenes: 130° C.,
c) experiments with 2-pentene: 120° C.

On attainment of the reaction temperature, the synthesis gas pressure was increased to 20 bar (50 bar for 1-octene) and the olefin was added. The reaction was conducted at constant pressure (closed-loop pressure controller from Bronkhorst, the Netherlands) over the reaction times specified in Table 1. After the experiment time had expired, the autoclave was cooled to room temperature, decompressed and purged with argon with stirring. In each case 1 ml of the reaction mixtures was withdrawn immediately after the stirrer had been switched off, diluted with 5 ml of pentane and analyzed by gas chromatography.

TABLE 1

Examples of hydroformylation with ligands (D), (E), (H) and (J)

| Ex. No. | Ligand | Olefin | Rh [ppm] | Olefin:Rh | T[°C.], p[bar], t[h] | Yield [%] | n-Selectivity [%] |
|---|---|---|---|---|---|---|---|
| 5 | (D) | 1-Octene | 28 | 7850 | 100, 50, 3 | 70 | 97.3 |
| 6* | (D) | 1-Octene | 14 | 15 700 | 100, 50, 3 | 56 | 97.5 |
| 7 | (D) | 2-Pentene | 140 | 621 | 120, 20, 6 | 74 | 86.6 |
| 8 | (D) | n-Octenes | 140 | 1570 | 130, 20, 6 | 40 | 81.1 |
| 9 | (E) | 1-Octene | 28 | 7850 | 100, 50, 3 | 87 | 85.3 |
| 10 | (E) | n-Octenes | 140 | 1570 | 130, 20, 6 | 76 | 59.4 |
| 11 | (H) | 1-Octene | 14 | 15 700 | 100, 50, 3 | 44 | 84.0 |
| 12 | (H) | 1-Octene | 28 | 7850 | 100, 50, 3 | 51 | 87.1 |
| 13 | (J) | 2-Pentene | 140 | 1570 | 120, 20, 3 | 34 | 86.8 |
| 14 | (J) | 1-Octene | 28 | 7850 | 100, 50, 3 | 84 | 86.0 |
| 15 | (J) | 2-Pentene | 140 | 1570 | 120, 20, 3 | 100 | 65.9 |
| 16 | (X) | 1-Octene | 40 | 12 613 | 120, 20, 3 | 46.2 | 92.4 |

* Ligand/rhodium ratio = 10:1

COMPARATIVE EXAMPLE 16

The hydroformylation experiment was performed in a 100 ml autoclave from Parr equipped with pressure-maintaining device, gas flow meter, stirrer and pressure pipette. For the experiments, a solution of the rhodium in the form of rhodium nonanoate as a catalyst precursor in toluene was introduced into the autoclave under an argon atmosphere: for experiments with 40 ppm by mass of rhodium, 3.1 ml of a 0.734 mM solution were used.

Subsequently, the appropriate amount of 5 ligand equivalents per rhodium of the phosphite compound X dissolved in toluene were added. Addition of further toluene adjusted the starting mass of the catalyst solution to 29 g for the reaction with 1-octene or the n-octenes (=mixture of 1-octene, 2-octene, 3-octene and 4-octene). 29 g of 1-octene or n-octenes were introduced into the pressure pipette. At a synthesis gas pressure of 11-13 bar with stirring (1000 rpm), the autoclave was heated to 120° C.

On attainment of the reaction temperature, the synthesis gas pressure was increased to 20 bar and the olefin was added. The reaction was conducted at constant pressure (closed-loop pressure regulator from Bronkhorst, the Netherlands) over the course of the reaction times specified in the table. After the experiment time had expired, the autoclave was cooled to room temperature, decompressed and emptied. During the reaction, samples were taken, diluted with 1 ml of pentane and analyzed by gas chromatography.

At 120° C., the comparative experiment gives rise to an n-selectivity which is comparable, for example, with Examples 1 and 2. In spite of the higher reaction temperature, the yield at 46.2% is significantly lower (Table 1).

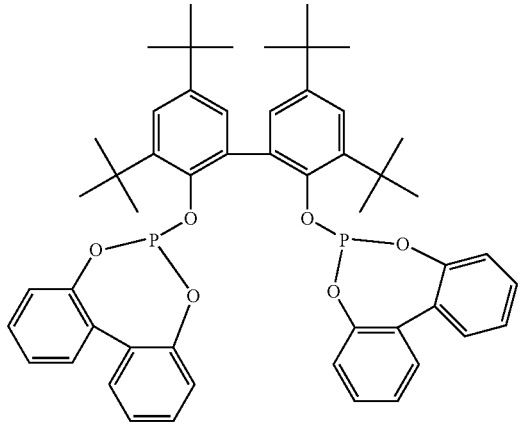

(X)

COMPARATIVE EXAMPLE 17

Analogously to Experiments 5 and 6, Example Experiments 5b and 6b were performed with a ligand of the formula Z. The preparation of the ligand Z can be taken, for example, from DE 100 53 272. In Examples 5b and 6b, lower n-selectivities are observed throughout than in the case of use of the inventive ligands (Table 2).

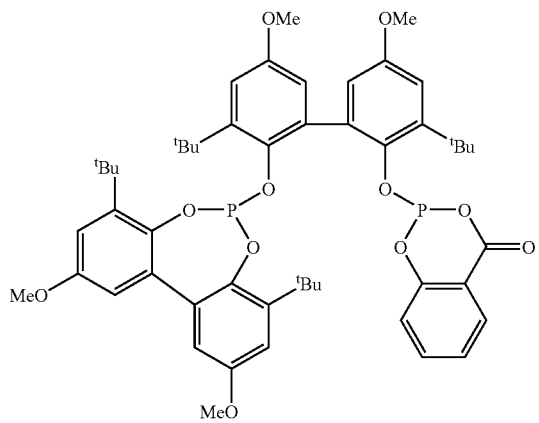

(Z)

TABLE 2

Comparative examples with ligand Z

| Ex. No. | Ligand | Olefin | Rh [ppm] | Olefin:Rh | T[° C.], p[bar], t[h] | Yield [%] | n-Selectivity [%] |
|---|---|---|---|---|---|---|---|
| 5b | Z | 1-Octene | 28 | 16 220 | 100, 50, 3 | 63.7 | 38.3 |
| 6b* | Z | 1-Octene | 14 | 31 563 | 100, 50, 3 | 61.5 | 43.8 |

*Ligand/rhodium ratio = 10:1

EXAMPLE 18

Preparation of Ligand (M)

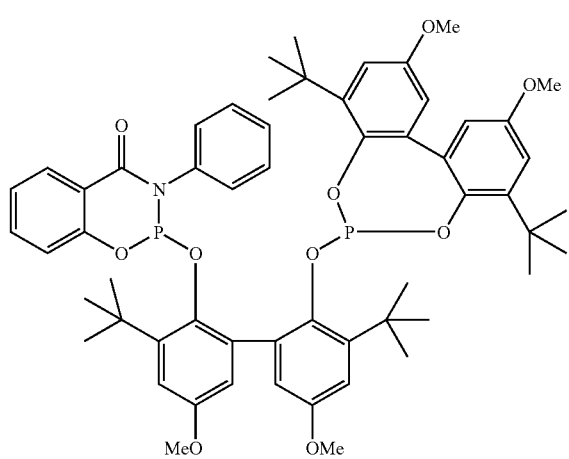

(M)

a) Preparation of the P—Cl Unit (Ω)

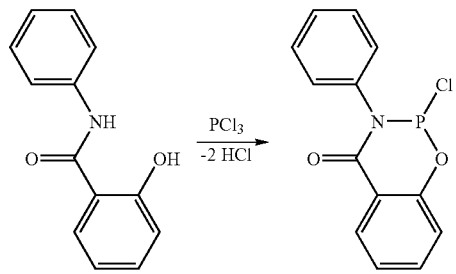

(Ω)

17.2 ml of a 2.73 M solution (46.85 mmol) of phosphorus trichloride in toluene are added dropwise at room temperature with stirring to a suspension of 9.99 g (46.85 mmol) of salizylanilide in toluene (42 ml). Subsequently, the mixture is heated under reflux for 5.5 h, filtered after cooling and concentrated to dryness under reduced pressure. The product (Ω) thus obtained is approx. 95% pure according to NMR spectroscopy findings and was used as obtained for the further synthesis. The purity can be increased further by a recrystallization from toluene. Yield: 12.23 g (93% of theory). $^{31}P\{^1H\}$ NMR (CD$_2$Cl$_2$): δ 139.6 ppm.

b) Preparation of the Hydroxyphosphite Compound (Δ)

For the preparation of (Δ), see the information on the synthesis of ligand (D).

c) Preparation of Ligand (M)

An equimolar amount of n-butyllithium in the form of a 0.32 M solution in hexane is added at −20° C. with stirring to a solution of 3.065 g (4.114 mmol) of the hydroxyphosphite (Δ) in THF (50 ml). The mixture is stirred for another 15 min, then allowed to warm to room temperature, and the solution thus obtained at 0° C. is added to a solution of 1.20 g (4.32 mmol, approx. 5% excess) of the Cl-phosphorus compound in THF (20 ml). After warming to room temperature, the mixture is stirred for 16 h and the solvent is removed under reduced pressure. The remaining residue is extracted first with 3×20 ml of hexane and then with 50 ml of boiling toluene. Concentration of the toluene filtrate by half, addition of 25 ml of hexane and storage at 5° C. for several days gives rise to a beige precipitate. The mixture is filtered, and the precipitate is washed with hexane (2×5 ml) and dried at bath temperature 60° C. in an oil-pump vacuum. Yield: 2.23 g (55%). Elemental analysis (calc. for C$_{57}$H$_{65}$O$_{10}$P$_2$N=986.08 g/mol): C, 70.49 (69.43); H, 6.64 (6.57); N, 1.38 (1.42)%. $^{31}P\{^1H\}$ NMR (CD$_2$Cl$_2$): δ 112.2, 113.8, 115.2, 140.1, 141.4, 143.2 ppm.

EXAMPLE 19

Preparation of Ligand (L)

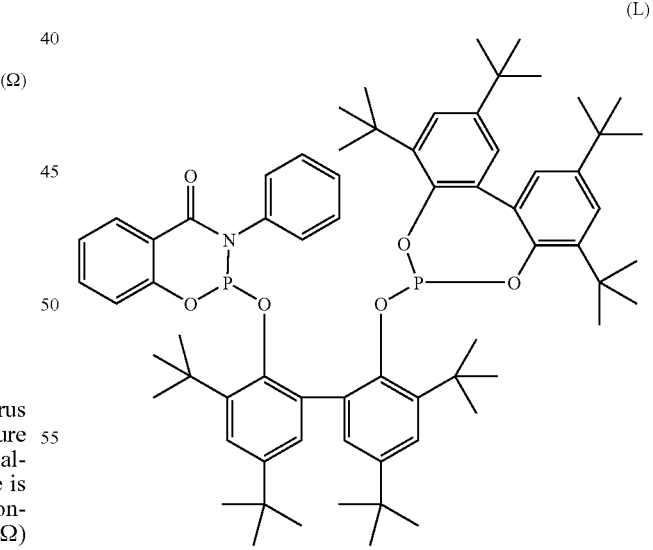

(L)

The preparation is effected analogously to ligand (M).

2.957 g (3.482 mmol) of the hydroxyphosphite (Σ) (see Example 3), an equimolar amount of n-butyllithium in the form of a 0.32 M solution and 1.015 g (3.656 mmol) of the Cl-phosphorus compound used for the synthesis of (M) are used. For workup, the reaction mixture is concentrated to dryness, the residue is stirred with hexane (65 ml) and filtered, and the solvent is removed under reduced pressure. Drying at bath temperature 60° C. in an oil-pump vacuum gives rise to 3.615 g (94%) of the target compound. Elemental analysis (calc. for $C_{69}H_{89}O_6P_2N=1090.41$ g/mol): C, 75.68 (76.00); H, 8.21 (8.23); N, 1.30 (1.29); P, 5.20 (5.68)%. $^{31}P\{^1H\}$ NMR ($CD_2Cl_2$): δ 112.4, 115.4, 141.9 ppm.

EXAMPLE 20

Preparation of Ligand (P)

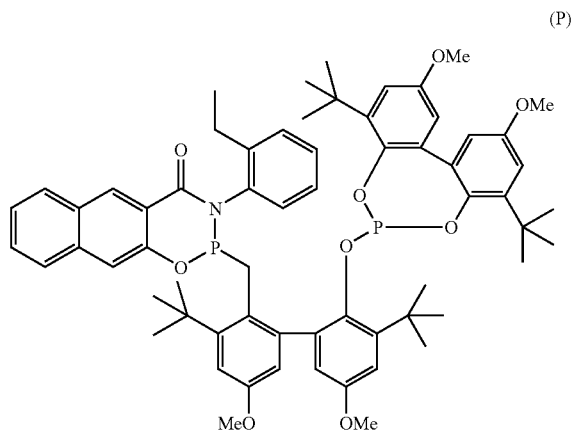

(P)

a) Preparation of the P—Cl Unit (Ξ)

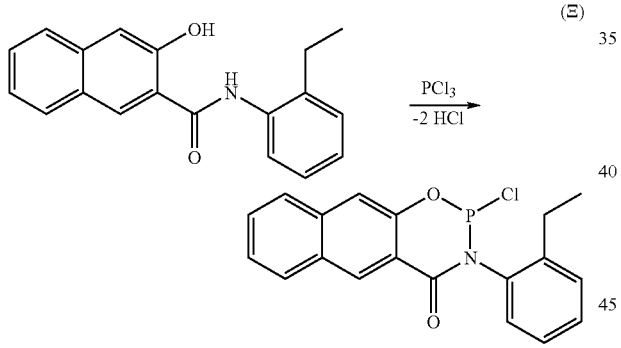

(Ξ)

18.5 ml of a 3.747 M solution (69.44 mmol) of phosphorus trichloride in toluene are added dropwise at room temperature with stirring to a suspension of 20.23 g (69.44 mmol) of 2'-ethyl-3-hydroxynaphthalene-2-carboxanilide in toluene (80 ml). The mixture is subsequently heated under reflux for 5 h and concentrated to dryness under reduced pressure. The brown residue formed is taken up in dichloromethane (60 ml). After filtration, the solvent is evaporated under reduced pressure and the residue is dissolved in warm toluene (50 ml). The crystal mass formed at 5° C. after storage for several days is filtered off, washed with cold toluene (10 ml) and dried in an oil-pump vacuum at bath temperature 60° C. The product thus obtained (Ξ) is pure by NMR spectroscopy. Yield: 13.18 g (60% of theory). Elemental analysis (calc. for $C_{19}H_{15}NO_2PCl=355.76$ g/mol): C, 64.48 (64.15); H, 4.13 (4.25); N, 3.89 (3.94); P, 8.73 (8.71); Cl, 9.88 (9.97)%. $^{31}P\{^1H\}$ NMR ($CD_2Cl_2$): δ 138.2, 139.4 ppm.

b) Preparation of the Hydroxyphosphite Compound (Δ)

For the preparation of (Δ), see the information on the synthesis of ligand (D).

c) Preparation of Ligand (P)

The reaction is performed with 3.078 g (4.133 mmol) of the hydroxyphosphite (Δ), 12.9 ml of a 0.32 M solution of n-butyllithium in hexane (4.133 mmol) and 1.47 g (4.133 mmol) of the Cl-phosphorus compound (Ξ). After the solvent has been distilled off under reduced pressure, the syrupy residue is extracted first with hot hexane (100 ml) and then at room temperature with toluene (40 ml). The hexane filtrate is concentrated by half and stored at room temperature for 3 days. The precipitate formed is filtered off, washed with cold hexane (10 ml) and dried at 60° C. under reduced pressure. The toluene filtrate is concentrated to dryness. The resulting solid is spectroscopically identical to that obtained from hexane. Yield: 2.42 g (55%). Elemental analysis (calc. for $C_{63}H_{71}NO_{10}P_2=1064.20$ g/mol): C, 71.05 (71.11); H, 7.01 (6.72); N, 1.42 (1.32); P, 5.55 (5.82)%. CI-MS (isobutane): m/e 1064 (18%, M$^+$), 783 (12%), 745 (85%), 677 (60%). $^{31}P\{^1H\}$ NMR ($CD_2Cl_2$): δ 112.2, 113.3, 113.8, 114.2, 115.6, 116.3, 139.8, 141.1, 141.6, 142.2, 143.0, 143.6 ppm

EXAMPLE 21

Preparation of Ligand (O)

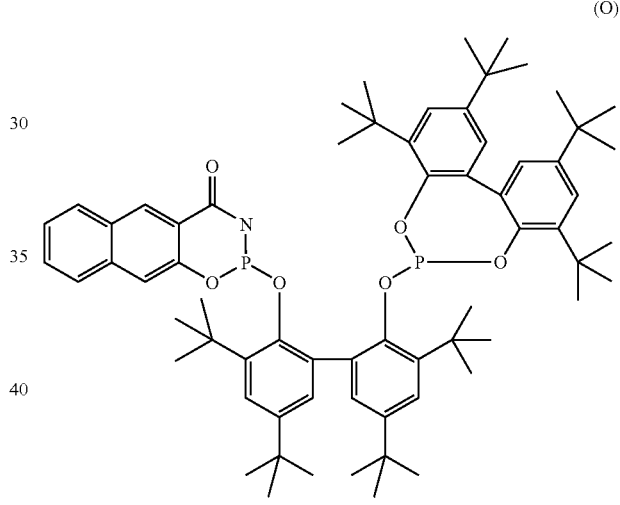

(O)

The reaction is performed with 3.144 g (3.7 mmol) of the hydroxyphosphite (Σ), 11.6 ml of a 0.32 M solution of n-butyllithium in hexane (3.7 mmol) and 1.316 g of the Cl-phosphorus compound (Ξ), initially analogously to the ligand (M). After stirring for 16 h at room temperature, the mixture is heated to 60° C. for another 5 h, then the solvent is removed under reduced pressure and the residue is taken up in hexane (60 ml) and filtered. Concentration of the solution to half the volume and leaving it to stand at 5° C. overnight gives rise to a crystalline precipitate which is filtered off, washed with 10 ml of cooled hexane and dried at 60° C. under reduced pressure. Yield: 3.05 g (71% of theory). Elemental analysis (calc. for $C_{75}H_{95}NO_6P_2=1168.52$ g/mol): C, 77.30 (77.09); H, 8.52 (8.19); N, 1.35 (1.20)%. CI-MS (isobutane): m/e 1168 (30%, M$^+$), 850 (51%), 833 (84%), 731 (81%), 441 (100%). $^{31}P\{^1H\}$ NMR ($CD_2Cl_2$): δ 112.6, 113.8, 118.9, 122.6, 142.2 ppm.

HYDROFORMYLATION EXPERIMENTS 22 TO 30

The experiments were preformed as above for ligands (D), (E), (H) and (J). For all experiments, 10 ml of the 6.04 mM solution of the rhodium starting compound were used, corresponding to about 140 ppm by mass of rhodium. The ligand/rhodium ratio was always 5 (see Table 3 for results).

COMPARATIVE EXAMPLES 31 TO 33

The experiments were performed as described above for Comparative Example 16. Experiment 31 gives rise to similar selectivities to Experiments 22 and 28. The yield for the catalyst with the ligand M (Experiment 22) is significantly higher than with the ligand X. Experiments 32 and 33 show examples with internal n-octenes as the reactant, in which selectivities of 81.9 (ligand X) and 83.9% (ligand Y) are achieved. The yield is about 16.9%. In comparison thereto, for example, with the inventive ligands M and P in the reaction of the internal 2-pentene (Experiments 23 and 29), both higher n-selectivities and significantly higher yields are obtained (Table 3).

TABLE 3

Examples of hydroformylation with ligands (M), (L), (O) and (P)

| Ex. No. | Ligand | Olefin | Olefin:Rh | T[° C.], p[bar], t[h] | Yield [%] | n-Selectivity [%] |
|---|---|---|---|---|---|---|
| 22 | (M) | 1-Octene | 1556 | 100, 20, 3 | 62 | 94.6 |
| 23 | (M) | 2-Pentene | 630 | 120, 20, 6 | 86 | 80.9 |
| 24 | (L) | 1-Octene | 1523 | 100, 20, 6 | 72 | 60.5 |
| 25 | (L) | 2-Pentene | 664 | 120, 20, 6 | 95 | 56.0 |
| 26 | (O) | 1-Octene | 1546 | 100, 20, 3 | 26 | 77.1 |
| 27 | (O) | 2-Pentene | 1570 | 120, 20, 6 | 3 | 65.9 |
| 28 | (P) | 1-Octene | 1540 | 100, 20, 3 | 45 | 92.4 |
| 29 | (P) | 1-Octene | 1550 | 80, 20, 6 | 55 | 97.1 |
| 30 | (P) | 2-Pentene | 632 | 120, 20, 6 | 27 | 77.6 |
| 31 | (X) | 1-Octene | 12613 | 120, 20, 3 | 46.2 | 92.4 |
| 32 | (X) | n-Octenes | 12 655 | 120, 20, 2, 5 | 15.0 | 81.9 |
| 33 | (Y) | n-Octenes | 12 161 | 120, 20, 3 | 16.9 | 83.9 |

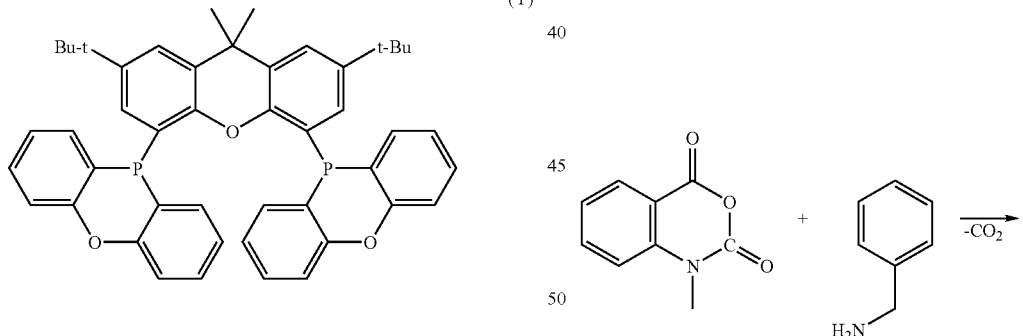

EXAMPLE 34

Preparation of Ligand (A)

a) Preparation of the P—Cl Unit (Ψ)

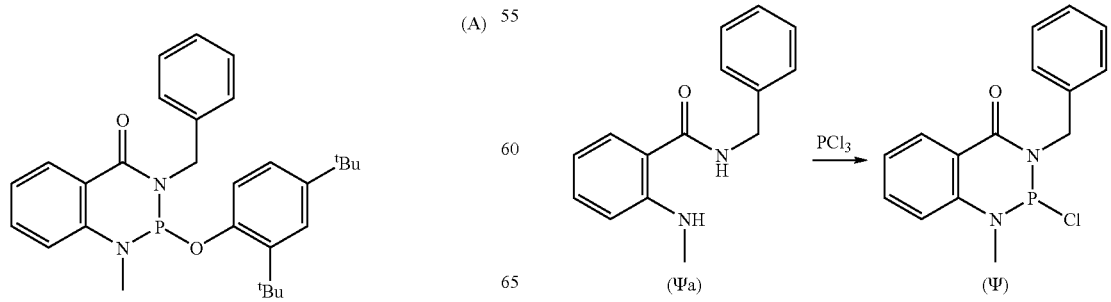

The synthesis was performed based on I. Neda et al., Z. Naturforsch. 49b, 1994, 788-800: 27.4 g (28 ml; 0.253 mol) of benzylamine (99%) were added dropwise within 20 min with stirring by means of a syringe to a solution of 30.2 g (0.153 mol) of N-methylisatoic anhydride (90%) in 300 ml of dioxane (dried) in a with 500 ml Schlenk tube. The resulting reaction mixture was heated to 70° C. with stirring and kept at this temperature for 8 hours. Overnight, the solution was cooled to room temperature. Thereafter, the entire reaction mixture was filtered through a frit. The very minor black precipitate (particles) on the frit was discarded. The solvent was distilled off from the filtrate by means of vacuum under reduced pressure. The residue was extracted with 120 ml of diethyl ether. The product (Ψa) crystallizes at −21° C. after storage for 24 hours. After filtration, the product was washed twice with 50 ml of pentane and then dried. Analysis: GC-MS: 27.33 min; m/e 240 (80%, M+), 134 (60%), 106 (100%).

In a purged 250 ml Schlenk tube, 12.1 g (0.05 mol) of (Ψa) and 10.1 g (14 ml) (0.1 mol) of triethylamine are dissolved in 175 ml of dried toluene. 6.9 g (4.4 ml) (0.05 mol) of phosphorus trichloride are added to the solution slowly and constantly at room temperature. This reaction mixture is stirred at 70° C. for 4 h and then cooled to room temperature. Subsequently, the triethylammonium chloride is filtered off and the solvent of the filtrate is distilled off in an oil-pump vacuum. An orange viscous oil is formed (Ψ). Analysis: GC-MS: 28.35 min; m/e 304 (100%, M+), 269 (100%), 199 (55%), 91 (100%); $^{31}$P{$^{1}$H} NMR (d$_8$-toluene): δ 127.9 ppm.

c) Preparation of Ligand (A)

A solution of 5.8 g (0.028 mol) of 2,4-di-tert-butylphenol and 6 g (=8.4 ml; 0.06 mol) of triethylamine in 100 ml of toluene is added dropwise at −20° C. to a solution of 8.6 g (0.1 mol) of (T) in 100 ml of toluene. After warming to room temperature within 14 h, the reaction mixture is filtered, the solution of the filtrate is removed in an oil-pump vacuum and the residue is recrystallized in acetonitrile. $^{31}$P{$^{1}$H} NMR (dg-toluene): δ 112.3 ppm.

HYDROFORMYLATION EXAMPLES 35 TO 37

The hydroformylation experiments were performed in a 100 ml autoclave from Parr equipped with pressure-maintaining device, gas flow meter, paddle stirrer and HPLC pump. 2.55 g of a solution of 0.357% by mass of rhodium nonanoate in toluene and 4.50 g of a solution of 2.204% by mass of ligand (Δ) in toluene were introduced into the autoclave under an argon atmosphere. The amount of toluene was supplemented to 30 g. Subsequently, the rhodium-ligand mixture was brought to a pressure of 5-10 bar (target pressure 20 bar) or 10-15 bar (target pressure 40 bar) with stirring (1000 rpm) with synthesis gas (1:1 CO/H2), and heated to 100° C. or 120° C. On attainment of the desired reaction temperature, 1-octene was added via an HPLC pump and the pressure was adjusted to the target pressure of 20 bar or 40 bar by closed-loop control. During the experiment run time, samples were taken at fixed intervals. The reaction was conducted at constant pressure (pressure regulator from Bronkhorst (the Netherlands)) over 5 h. Once the experiment time had expired, the autoclave was cooled to room temperature, decompressed and purged with argon. In each case 0.2 ml of the autoclave solution was admixed with 0.8 ml of n-pentane and analyzed by gas chromatography.

TABLE 4

Examples of hydroformylation with (A)

| Ex. No. | Ligand | Olefin | Rh [ppm], Ligand/Rh | T[° C.], p[bar], t[h] | Yield after 3 h [%] | Yield after 5 h [%] | n-Selectivity after 3 h [%] | n-Selectivity after 5 h [%] |
|---|---|---|---|---|---|---|---|---|
| 35 | (A) | 1-Octene | 40, 10/1 | 120, 20, 5 | 71 | 89 | 35.4 | 34.5 |
| 36 | (A) | n-Octenes | 40, 10/1 | 120, 20, 5 | 48 | 70 | 44.6 | 32.3 |
| 37 | (A) | n-Butenes | 40, 10/1 | 120, 20, 5 | 88 | 96 | 32.5 | 55.4 |
| 38 | PPh$_3$ | 1-Octene | 40, 10/1 | 120, 20, 3 | 54.7 | — | 47.3 | — |
| 39 | PPh$_3$ | n-Octenes | 40, 10/1 | 120, 20, 3 | 4.3 | — | 29.7 | — |
| 40 | PPh$_3$ | n-Butenes | 40, 10/1 | 120, 20, 3 | 65.2 | — | 40.9 | — |

COMPARATIVE EXAMPLES 38 to 40

The experiments were performed as described above for Comparative Example 16. Triphenylphosphine was used as the ligand. Experiment 35, in which 1-octene is reacted, gives rise to a higher yield than Comparative Example 38 with the inventive ligand. In Experiment 36 in which n-octenes are reacted, both the yield and the n-selectivity are significantly enhanced compared to Comparative Experiment 39. The yield with n-butenes as the reactant (Experiment 37) is significantly enhanced compared to Experiment 40 (Table 4).

The invention claimed is:

1. A process for hydroformylating olefins, comprising:
   reacting a monoolefin or a monoolefin mixture having from 2 to 25 carbon atoms with a mixture of carbon monoxide and hydrogen in the presence of a heteroacylphosphite of general formula (1) or a corresponding complex with one or more metals of groups 4 to 10 of the Periodic Table of the Elements

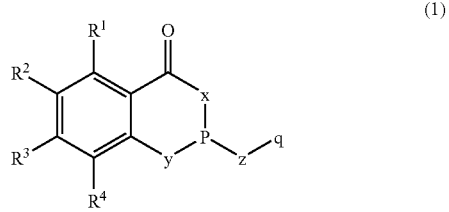

(1)

wherein R$^1$, R$^2$, R$^3$, R$^4$ and q are the same or different and are each a substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 70 carbon atoms, H, F, Cl, Br, I, —CF$_3$, —CH$_2$(CF$_2$)$_j$CF$_3$ wherein j=0-9, —OR$^5$, —COR$^5$, —$CO_2R^5$, —$CO_2M$, —$SiR^5_3$, —$SR^5$, —$SO_2R^5$, —$SOR^5$, —$SO_3R^5$, —$SO_3M$, —$SO_2NR^5R^6$, —$NR^5R^6$, —$N=CR^5R^6$, wherein $R^5$ and $R^6$ are the same or different and are each as defined for $R^1$, and M is an alkali metal, an alkaline earth metal ion which is present in the formula as one half, an ammonium or phosphonium ion, x, y, z are each independently O, $NR^7$, S, where $R^7$ is as defined for q, and x, y, z are not simultaneously O, with the proviso that when q is a radical which has a structural formula (6c)

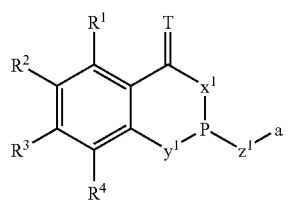

(6c)

wherein the $R^1$ to $R^4$ radicals are each as defined for formula (1), $x^1$, $y^1$, $z^1$ are each independently O, $NR^7$, S, where $R^7$ is as defined for q, T is an oxygen or an $NR^{30}$ radical, wherein $R^{30}$ is as defined for q, and the a position serves as the attachment point, x and $x^1$ must not simultaneously be N, and x must not be N when T is $NR^{30}$.

2. The process as claimed in claim 1, wherein the $R^1$ and $R^2$, $R^2$ and $R^3$ and/or $R^3$ and $R^4$ radicals form a fused substituted or unsubstituted aromatic, heteroaromatic, aliphatic, mixed aromatic-aliphatic or mixed heteroaromatic-aliphatic ring system.

3. The process as claimed in claim 1, wherein the q radical consists of the W-R radicals wherein W is a divalent substituted or unsubstituted aliphatic, alicyclic, mixed aliphatic-alicyclic, heterocyclic, mixed aliphatic-heterocyclic, aromatic, heteroaromatic, mixed aliphatic-alicyclic, hydrocarbon radical having from 1 to 50 carbon atoms, and the R radical is —$OR^5$, —$NR^5R^6$, phosphite, phosphonite, phosphinite, phosphine or heteroacylphosphite of formula (6c), wherein $R^5$ and $R^6$ are the same or different and are as defined for $R^1$.

4. The process as claimed in claim 3, wherein
W is a radical of general formula (2)

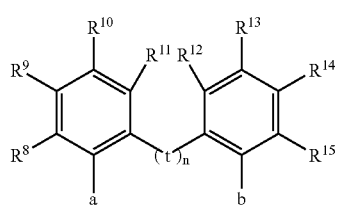

(2)

where $R^8$, $R^9$, $R^{10}$, $R^{11}$, $R^{12}$, $R^{13}$, $R^{14}$ and $R^{15}$ are the same or different and are each as defined for $R^1$, t is a divalent $CR^{16}R^{17}$, $SiR^{16}R^{17}$, $NR^{16}$, O or S radical, and $R^{16}$ and $R^{17}$ are each as defined for $R^5$ and $R^6$, n=0 or 1 and the a and b positions serve as attachment points.

5. The process as claimed in claim 4, wherein in each case two adjacent $R^9$ to $R^{15}$ radicals together or a fused substituted or unsubstituted, aromatic, heteroaromatic, aliphatic, mixed aromatic-aliphatic or mixed heteroaromatic-aliphatic ring system.

6. The process as claimed in claim 4, wherein W is a radical of general formula (3):

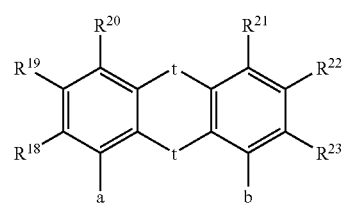

(3)

wherein $R^{18}$, $R^{19}$, $R^{20}$, $R^{21}$, $R^{22}$ and $R^{23}$ are the same or different and are each as defined for $R^1$, t is a divalent $CR^{16}R^{17}$, $SiR^{16}R^{17}$, $NR^{16}$, O or S radical, and $R^{16}$ and $R^{17}$ are each as defined for $R^5$ and $R^6$, n=0 or 1 and the a and b positions serve as attachment points.

7. The process as claimed in claim 6, wherein in each case two adjacent $R^{18}$ to R23 radicals together form a fused substituted or unsubstituted, aromatic, heteroaromatic, aliphatic, mixed aromatic-aliphatic or mixed heteroaromatic-aliphatic ring system.

8. The process as claimed in claim 3, wherein
W is a radical of general formula (4):

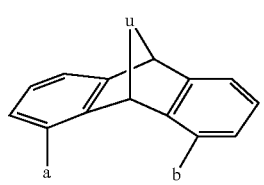

(4)

wherein u is a divalent group selected from radicals of formulae (5a), (5b) and (5c)

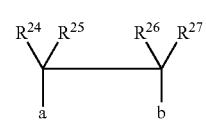

(5a)

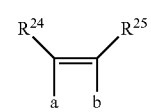

(5b)

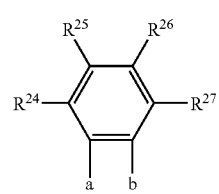

(5c)

in which $R^{24}$, $R^{25}$, $R^{26}$ and $R^{27}$ are the same or different are each as defined for $R^1$, and the a and b positions serve as attachment points.

9. The process as claimed in claim 8, wherein two adjacent $R^{24}$ to $R^{27}$ radicals together form a fused substituted or unsubstituted, aromatic, heteroaromatic, aliphatic, mixed aromatic-aliphatic or mixed heteroaromatic-aliphatic ring system.

10. The process as claimed in claim 3, wherein
R represents radicals of general formulae (6a), (6b) and (6c):

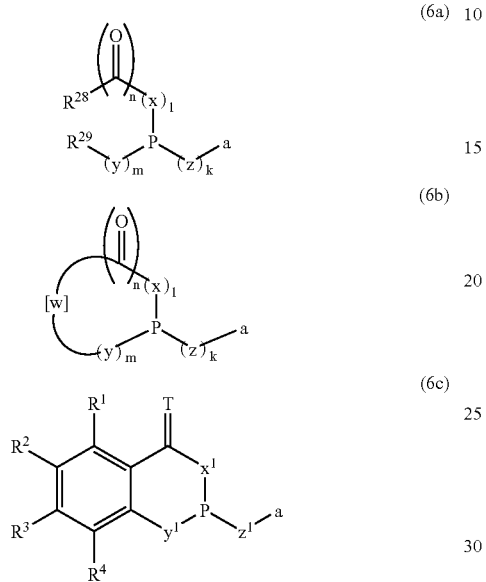

wherein $R^{28}$ and $R^{29}$ are the same or different and are each as defined for $R^1$,
x, y, z and W are each defined as specified and
m=0 or 1, n=0 or 1, k=0 or 1, l=0 or 1,
and the position a serves as the attachment point.

11. The process as claimed in claim 1, wherein the metal of groups 4 to 10 of the Periodic Table is selected from the group consisting of rhodium, platinum, palladium, cobalt and ruthenium.

12. The process as claimed in claim 1, wherein further phosphorus ligands are present.

13. A process for making a compound, wherein said process comprises:
hydrocyanation, isomerization of an olefin or amidocarbonylation and wherein said process is conducted in the presence of heteroacylphosphines of formula (1)

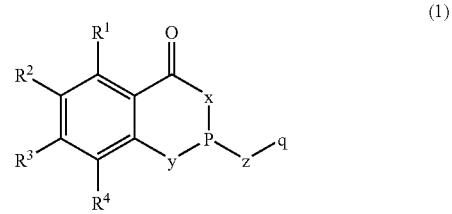

or metal complexes thereof,
wherein $R^1$, $R^2$, $R^3$, $R^4$ and q are the same or different and are each a substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 70 carbon atoms, H, F, Cl, Br, I, $-CF_3$, $-CH_2(CF_2)_jCF_3$ wherein j=0-9, $-OR^5$, $-COR^5$, $-CO_2R^5$, $-CO_2M$, $-SiR^5_3$, $-SR^5$, $-SO_2R^5$, $-SOR^5$, $-SO_3R^5$, $-SO_3M$, $-SO_2NR^5R^6$, $-NR^5R^6$, $-N=CR^5R^6$, wherein $R^5$ and $R^6$ are the same or different and are each as defined for $R^1$, and M is an alkali metal ion, an alkaline earth metal ion, which is present in the formula as one half, an ammonium or phosphonium ion, x, y, z are each independently O, $NR^7$, S, wherein $R^7$ is as defined for $R^1$.

14. A process for carbonylation wherein the carbonylation is carried out in the presence of a heteroacylphosphite of formula (1)

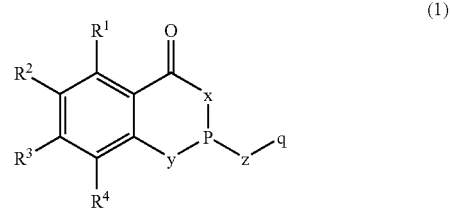

or metal complexes thereof,
where $R^1$, $R^2$, $R^3$, $R^4$ and q are the same or different and are each a substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 70 carbon atoms, H, F, Cl, Br, I, $-CF_3$, $-CH_2(CF_2)_jCF_3$ where j=0-9, $-OR^5$, $-COR^5$, $-CO_2R^5$, $-CO_2M$, $-SiR^5_3$, $-SR^5$, $-SO_2R^5$, $-SOR^5$, $-SO_3R^5$, $-SO_3M$, $-SO_2NR^5R^6$, $-NR^5R^6$, $-N=CR^5R^6$, wherein $R^5$ and $R^6$ are the same or different and are each as defined for $R^1$, and M is an alkali metal ion, an alkaline earth metal ion which is present in the formula as one half, an ammonium or phosphonium ion, x, y, z are each independently 0, $NR^7$, S, where $R^7$ is as defined for q, and x, y, z are not simultaneously 0, with the proviso that when q has a radical which has a structural formula (6c)

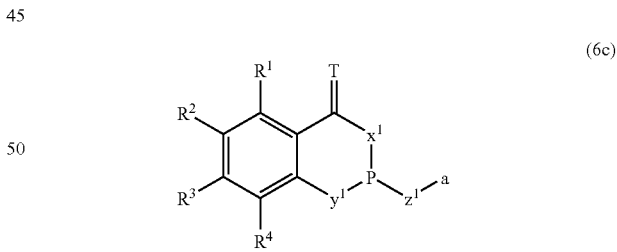

wherein the $R^1$ to $R^4$ radicals are each as defined for formula (1), $x^1$, $y^1$, $z^1$ are each independently O, $NR^7$, S, where $R^7$ is as defined for q, T is an oxygen or an $NR^{30}$ radical, wherein $R^{30}$ is as defined for q, and the a position series as the attachment point, x and $x^1$ must not simultaneously be N and x must not be N when T is $NR^{30}$.

* * * * *